US005567688A

United States Patent [19]

Chu et al.

[11] Patent Number: 5,567,688
[45] Date of Patent: Oct. 22, 1996

[54] L-NUCLEOSIDES FOR THE TREATMENT OF HEPATITIS B-VIRUS

[75] Inventors: Chung K. Chu, Athens, Ga.; Yung-Chi Cheng, Woodbridge, Conn.; Balakrishna S. Pai, New Haven, Conn.; Gang-Oing Yao, Guilford, Conn.

[73] Assignees: Univ. of GA Research Foundation, Athens, Ga.; Yale University, New Haven, Conn.

[21] Appl. No.: 467,010

[22] Filed: Jun. 6, 1995

Related U.S. Application Data

[63] Continuation of Ser. No. 189,070, Jan. 28, 1994.

[51] Int. Cl.$^6$ .................................................. A61K 31/70
[52] U.S. Cl. ............................ 514/46; 514/47; 514/49; 514/50; 514/51; 514/893; 514/894; 536/26.26; 536/26.7; 536/26.8; 536/27.6; 536/28.5; 536/28.54; 536/28.55; 424/420; 424/457
[58] Field of Search ........................... 514/45, 46, 49, 514/50, 893, 894, 51, 47; 536/28.54, 28.55, 27.6, 26.26, 26.7, 26.8, 28.5, 28.54, 28.55; 424/420, 457

[56] References Cited

U.S. PATENT DOCUMENTS

| | | | |
|---|---|---|---|
| 3,116,268 | 12/1963 | Hunter | 528/337 |
| 3,553,192 | 1/1971 | Gauri | 536/28.54 |
| 4,000,137 | 12/1976 | Dvonoch et al. | 544/277 |
| 4,336,381 | 6/1982 | Nagata et al. | 544/313 |
| 4,861,759 | 8/1989 | Mitsuya et al. | 514/46 |
| 4,879,277 | 11/1989 | Mitsuya et al. | 514/49 |
| 4,900,828 | 2/1990 | Belica et al. | 544/317 |
| 4,918,122 | 4/1990 | Chu et al. | 514/50 |
| 4,963,533 | 10/1990 | de Clercq et al. | 514/49 |
| 4,968,674 | 11/1990 | Tanlyama et al. | 514/49 |
| 5,041,449 | 8/1991 | Belleau et al. | 514/274 |
| 5,047,407 | 9/1991 | Belleau et al. | 514/274 |
| 5,059,690 | 10/1991 | Zahler et al. | 544/276 |
| 5,071,983 | 12/1991 | Koszalka et al. | 544/317 |
| 5,089,500 | 2/1992 | Daluge | 514/261 |
| 5,151,426 | 9/1992 | Belleau et al. | 514/262 |
| 5,179,104 | 1/1993 | Chu et al. | 544/310 |
| 5,185,437 | 2/1993 | Koszalka et al. | 536/27.14 |
| 5,204,466 | 4/1993 | Liotta et al. | 544/317 |
| 5,210,085 | 5/1993 | Liotta et al. | 514/274 |
| 5,215,971 | 6/1993 | Datema et al. | 514/49 |
| 5,234,913 | 8/1993 | Furman, Jr. et al. | 514/49 |
| 5,246,924 | 9/1993 | Fox et al. | 514/50 |
| 5,248,776 | 9/1993 | Chu et al. | 544/310 |
| 5,270,315 | 12/1993 | Belleau et al. | 514/262 |
| 5,276,151 | 1/1994 | Liotta | 544/317 |
| 5,409,906 | 4/1995 | Datema et al. | 514/49 |
| 5,432,165 | 7/1995 | Adair et al. | 514/50 |
| 5,444,063 | 8/1995 | Schinazi | 514/262 |
| 5,446,029 | 8/1995 | Eriksson et al. | 514/45 |
| 5,466,806 | 11/1995 | Belleau et al. | 544/310 |

FOREIGN PATENT DOCUMENTS

| | | |
|---|---|---|
| 0206497 | 12/1986 | European Pat. Off. . |
| 0217580 | 4/1987 | European Pat. Off. . |
| 0285884 | 10/1988 | European Pat. Off. . |
| 0337713 | 10/1989 | European Pat. Off. . |
| 0433898 | 12/1989 | European Pat. Off. . |
| 0352248 | 1/1990 | European Pat. Off. . |
| 0375329 | 6/1990 | European Pat. Off. . |
| 0382526 | 8/1990 | European Pat. Off. . |
| 0494119 | 7/1992 | European Pat. Off. . |
| 0515144 | 11/1992 | European Pat. Off. . |
| 0515158 | 11/1992 | European Pat. Off. . |
| 0515157 | 11/1992 | European Pat. Off. . |
| 0526253 | 2/1993 | European Pat. Off. . |
| WO88/07532 | 10/1988 | WIPO . |
| WO88/08001 | 10/1988 | WIPO . |
| WO90/12023 | 10/1990 | WIPO . |
| WO91/11186 | 8/1991 | WIPO . |
| WO91/17159 | 11/1991 | WIPO . |
| WO92/06102 | 4/1992 | WIPO . |
| WO92/08727 | 5/1992 | WIPO . |
| WO92/10496 | 6/1992 | WIPO . |

(List continued on next page.)

OTHER PUBLICATIONS

Asseline, U., et al., "Synethesis and Physiocochemical Properties of Oligonucleotides Built with Either α-L or β-L Nucleotides Units and Covalently Linked to an Acridine Derivative," *Nucleic Acids Research*, 19(15):4067–4074 (1991).

Balzarini, J., et al., "Potent and Selective Anti–HTLV–III/ LAV Activity of 2',3'-Dideoxycytidinene, . . . ," *Bloch. and Bioph. Res. Comm.* 140(2):735–742 (1986).

Beach, J. W., et al., "Synthesis of EnantiomericallyPure (2'R,5'S)–(–)–1–[2–(hydroxymethyl)–oathiolan–5–yl]Cytosine . . . ," *J. Org. Chem*, 57:2217–2218 (1992).

Belleau, B., et al., "Design and Activity of a Novel Class of Nucleoside Analogs . . . ," *Intl. Conf. on AIDS*, Montreal, Quebec, Canada, Jun. 4–9, 1989.

Bouffard, D. Y., et al., "Kinetic Studies on 2',2'-Difluorodeoxycytidine(Gemcitibine) with Purified Human Deoxycytidine Kinase and Cytidine Deaminase," *Biochem. Pharmacol.* 45(9):1857–1861 (1993).

(List continued on next page.)

*Primary Examiner*—James O. Wilson
*Attorney, Agent, or Firm*—Cheryl K. Zalesky; Kilpatrick & Cody

[57] ABSTRACT

A method for the treatment of a human infected with HBV that includes administering an HBV-treatment amount of an L-nucleoside of the formula:

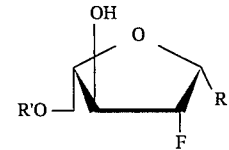

wherein R is selected from the group consisting of 5-methyluracil, adenine and cytosine, and R' is hydrogen, acyl, alkyl or a monophosphate, diphosphate or triphosphate ester, or its pharmaceutically acceptable salt.

32 Claims, 7 Drawing Sheets

FOREIGN PATENT DOCUMENTS

| | | |
|---|---|---|
| WO92/10497 | 6/1992 | WIPO. |
| WO92/14729 | 9/1992 | WIPO. |
| WO92/14743 | 9/1992 | WIPO. |
| WO92/15308 | 9/1992 | WIPO. |
| WO92/18517 | 10/1992 | WIPO. |
| WO92/21676 | 12/1992 | WIPO. |
| WO94/14456 | 7/1994 | WIPO. |
| WO94/14802 | 7/1994 | WIPO. |
| WO94/27618 | 12/1994 | WIPO. |
| WO95/07086 | 3/1995 | WIPO. |
| WO95/07287 | 3/1995 | WIPO. |
| WO95/18137 | 7/1995 | WIPO. |
| WO95/20595 | 8/1995 | WIPO. |
| WO95/21183 | 8/1995 | WIPO. |

OTHER PUBLICATIONS

Carter, et al., "Activities of (−)-Carbovlr and 3'-Azido-3'-Deoxythymidine Against Human Immunodeficiency Virus in Vitro," *Antimicrobial Agents and Chemotherapy*, 34(6):1297–1300 (1990).

Chang, C–N., et al., "Biochemical Pharmacology of (+) and (−)-2',3'-Dideoxy-3'Thioacytidine as Anti–Hepatitis B Virus Agents," *J. Biol. Chem.* 267(31):22414–22420 (1992).

Chang, Chien–Neng, et al., "Deoxycytidine Deaminase-resistant Steroisomer is the Active Form of . . . ," *J. Bio. Chem.*, 267(20):13938–13942 (1992).

Chang, Chungming, et al., "Production of Hepatitis B Virus in vitro by Transient Expression . . . ," *The Embo J.* 6(3):675–680 (1987).

Chen, Chin–Ho, et al., "Delayed Cytotoxicity and Selective Loss of Mitochondrial DNA in Cells . . . ," J. Bio. Chem. 264(20):11934–11937 (1989).

Cheng, Y. C., et al., "Human Deoxycytidine Kinase Purification and Characterization . . . ," *Biochim. Biophys. Acta.* 481:481–492 (1977).

Chottiner, E. G., "Cloning and Expression of Human Deocytctidine Kinase cDNA," *Proc. Natl. Sci. USA*, 88:1531–1535 (1991).

Chu, C. K., et al., "An Efficient Total Synthesis of 3'–Azido–3'–Deoxythlymidine (AZT) and 3'–Azido–2', 3'–Dideoxyuridine (AZDDU, CS–87) . . . ," *Tetrahedron Lett.*, 29(42):5349–5352 (1988).

Chu, et al., "Comparative Activity of 2',3'–Saturated and Unsaturated Pyrimidine and Purine Nucleosides . . . ," *Biochem. Pharm.* 37(18):3543–3548 (1988).

Chu, et al., "Structure–Activity Relationships of Pyrimidine Nucleosides as Antiviral Agents . . . ," *J. Med. Chem.* 32:612–617 (1989).

Chu, C. K., et al., "2'–Fluoro–5–Methyl–β–L–Arabinofuranosyluracil as a Novel Antiviral Agent for Hepatitis B . . . ," *Antimicrob. Agents Chemother.*, 39(4):979–981 (1995).

Coates, J., et al., "The Separated Enaniomers of 2'–deoxy–3'–thiacytidine (BCH–189) . . . ," *Antimicrob. Agents Chemother.* 36(1):202–205 (1992).

Cretton, E., et al. "Catabolism of 3'–Azido–3'–Deoxythymidine in Heptaocytes and Liver Microsomes . . . ," *Molecuilar Pharmacology*, 39:258–266 (1991).

Cretton, E., et al., "Pharmokinetics of 3'–Azido–3'–Dexoythimidine . . . ," *Antimicrobial Agents and Chemotherapy*, 35(5):801–807 (1991).

Di Bisceglie, Adrian M., Rustgi, Vinod K. et al., "Hepatocellular Carcinoma," NIH Conference, *Annals of Internal Medicine*, 108:390–401 (1988).

Doong, Shin–Lian., et al., "Inhibition of the Replication of Hepatitis B Virus in vitro . . . ," *Natl. Acad. Sci. USA*, 88:8495–8499 (1991).

Evans, David A., et al., "New Procedure for the Direct Generation of Titanium Enolates . . . ," *J. Am. Chem. Soc.*, 112:8215–8216 (1990).

Finlay, G. J., et al., "A Semiautomated Microculture Method for Investigating Exponentially Growing Carcinoma Cells," *Anal. Biochem.*, 139:272–277 (1984).

Furman, et al., "The Anti–Hepatitis B Virus Activities, Cytotoxicities, and Anabolic Profiles . . . ," Antim. Agents and Chemo., 36(12):2686–2692 (1992).

Ganem, Don et al., "The Molecular Biology of the Hepatitis B Viruses," *Ann. Rev. Biochem.*, 56:651–693 (1987).

Gosselin, G., "Enantiomeric 2',3'–Deoxycytidine Derivatives are Potent Human Immunodeficiency Virus Inhibitors in Cell Cultures," *C. R. Acad. Sci. Paris Sci. Vie.* 317: 85–89 (1994).

Jeong, L., et al., "Asymmetric Synthesis and Biological Evaluation of β–L–(2R,5S)–and a–L–(2R–5R)–1,3–Oxatholane–Pyrimidine and –Purine Nucleosides and Potential Anti–HIV Agents," *J. Med. Chem.*, 36(2):181–195 (1993).

Kassianides, Chris, et al., "Inhibition of Duck Hepatitis B Virus Replication by 2',3'–Dideoxycytidine," *Gastroenterology*, 97(5):1275–1280 (1989).

Kim, H. O., et al., "Potent Anti–HIV and Anti–HBV Activities of (−)–L–β–Dioxolane–C . . . ," *Tetrahedron Lett.*, 33(46):6899–6902 (1992).

Kim, H. O., et al., "L–β–(2S,4S)–and L–α–(2S,4R)–Dioxolanyl Nucleosides as Potential Anti–HIV Agents: . . . ," *J. Med. Chem.*, 36(5):519–528 (1993).

Kim, H. O., et al., "1,3–Dioxolanylpurine Nucelosides (2R, 4R)and (2R,4S) with Selective Anti–HIV–1 Activity . . . ," *J. Med. Chem. 36(1):30–37 (1993).*

Krenitsky, T. A., et al., "3'–Amino–2',3'–Dideoxyribonucleosides of Some Pyrimidines: Synthesis and Biological Activities," *J. Med. Chem.*, 26(6)891–895 (1983).

Kukhanova, M., et al., "L–and D–Enantiomers of 2',3'–Dideoxycytidine 5'–Triphosphate Analogs as Substrates for Human DNA Polymerases," *J. Bio. Chem.*, 270(39):23056–23059 (1995).

Lee, Bonita, et al., "In Vitro and In Vivo Comparison of the Abilities of Purine and . . . ," *Antimicrobial Agents and Chemotherapy*, 33(3):336–339 (1989).

Lin, T. S., et al., "Antiviral Activity of 2',3'–Dideoxy–β— L—5—fluorocytidiine(β–L–FddC) Against Hepatitis B Virus . . . ," 1:65–68 (1991).

Lin, et al., "Potent and Selective in Vitro Activity of 3'–Deoxythmindine–2–Ene–. . . ," *Biochem. Pharm.*, 36(17):2716 (1987).

Mansuri, M. M., et al., "Preparation of the Geometric Isomers of DDC, DDA, D4C, and D4T . . . ," *Bioorg. Med. Chem. Lett.*, 1:65–68 (1991).

Matthes, E., et al., "Potent Inhibition of Hepatitis B Virus Production in Vitro by Modified . . . ," *Anti. Agents and Chemot.*, 34(10):1986–1990 (1990).

Miller, Roger H., et al., "Common Evolutionary Origin of Hepatitis B Virus and Retroviruses," *Proc. Natl. Acad. Sci. USA*, 83:2531–2535 (1986).

Mitsuya, H., et al., "3'–Azido–3'–Deoxythymidine (BW A 509U): An Antiviral Agent that Inhibits . . . ," *Proc. Natl. Acad. Sci. USA*, 82:7097–7100 (1985).

Mitsuya, H., et al., "Rapid in Vitro Systems for Assessing . . . ," *AIDS: Modern Concepts and Therapeutic Challenges*, S. Broder, Ed. pp. 303, Marcel–Dekker, New York (1987).

Mitsuya, H., et al., "Molecular Targets for AIDS Therapy," *Science*, 249:1533–1544 (1990).

Norbeck, D., et al., "A New 2',3'–Dideoxynucleoside Prototype with in Vitro Activity Against HIV," *Tetrahedron Lett.*, pp. 6263–6266 (1989).

Okabe, M., et al., "Synthesis of the Dideoxynucleosides ddC and CNT . . . ," *J. Org. Chem.*, 53(20):4780–4786 (1988).

Onetto, M., et al., "In vitro Biochemical Tests to Evaluate the Response to Therapy of Acute Leukemia with . . . ," *Semin. Oncol.* 14(12), Suppl., pp. 231–237 (1987).

Pal, S. B., et al., "Inhibition of Hepatitis B Virus by a Novel L–Nucleoside, 2'–Fluoro–5–Methyl–β–L–Arabinofuranosyl Uracil," *Antimicrobial Agents and Chemotherapy*, 40(2):380–386 (1996).

Richman, D. D., et al., "The Toxicity of Azidothymidine (AZT) in the Treatment of Patients with AIDS . . . ," *N. Eng. J. Med.*, 317(4):192–197 (1987).

Ryan, K. J. et al., "9–β–L–Ribofuranosyladenine (L–Adenosine)", *Synthetic Procedures in Nucleic Acid Chemistry*, vol. 1, pp. 163–167, Interscience Publishers, New York, NY (1968).

Satsumabayashi, S. et al., "The Synthesis of 1,3–Oxathiolane–5–one Derivatives," *Bull, Chem. Soc. Japan*, 45:913–915 (1972).

Schinazi, R. F., et al., "Activities of the Four Optical Isomers of 2',3'–Dideoxy–3'–Thiacytidine . . . ," *Antimic. Agents & Chemo.*, 36(3):672–676 (1992).

Schinazi, R. F., et al., "Insights Into HIV Chemotherapy," *AIDS Research and Human Retroviruses* 8(6):963–989 (1992).

Schinazi, R. F. et al., "Pharmacokinetics and Metabolism of Racemic 2',3'–Dideoxy–5 . . . ," *Antimicrobial Agents and Chemotherapy* 36(11):2432–2438 (1992).Schinazi, R. F., et al., "Selective Inhibition of Human Immunodeficiency Viruses . . . ," *Antim. Agents and Chemo.*, 36(11):2423–2431 (1992).

Schinazi, R. F., et al., "Rapid Communications: Substrate Specificity of *Escherichia coli* . . . ," *Bloch. Pharm.*, 44(2):199–204 (1992).

Sells, Mary Ann, et al., "Production of Hepatitis B Virus Particles in Hep G2 Cells . . . ," *Proc. Natl. Acad. Sci. USA*, 84:1005–1009 (1987).

Soudeyns, H., et al., "Anti–Human Immunodeficiency Virus Type 1 Activity and In . . . ," *Antimicrobial Agents and Chemotherapy*, 35(7):1386–1390 (1991).

Spadari, S., et al., "L–Thymidine Is Phosphorylated by Herpes Simplex Virus Type 1 . . . ," *J. Med. Chem.*, 36(22):4214–4220 (1992).

Sterzycki, R. Z., et al., "Synthesis and Anti–HIV Activity of Several 2'–Fluoro–Containing Pyrimidine Nucleosides," *J. Med. Chem., 33(8):2150–2157 (1990)*.

Storer, R., et al., "The Resolution and Absolute Stereochemistry of the Enantiomeris of cis–1–[2–(Hydromethyl)–1, 3–Oxathiolan–5–yl)cytosine . . . ," *Nucleosides & Nucleotides, 12(2):225–236 (1993)*.

Sureau, C., et al., "Production of Hepatitis B Virus by a Differentiated Human Hepatoma Cell Line after Transfection with Cloned Circular HBV DNA," *Cell*, 47:37–47 (1988

Su, Tsann–Long, et al., "Nucleosides. 136, Synthesis and Antiviral Effects of Several 1–(2–Deoxy–2–Fluoro–β–D–Arabinofuranosyl)–5–Alkyluraclls, Some Structure–Activity Relationships, *J. Med. Chem.*, 29(1):151–154 (1986).

Tann, Chou H., et al., "Fluorocarbohydrates in Synthesis. An Efficient Synthesis of 1–(2–Deoxy–2–Fluoro–β–D–Arabino–Furanosyl)–5–Iodouracll (β–FIAU) and 1–(2–Deoxy–2–Fluoro–β–D–Arabinofuranosyl)thymine (β–FMAU).

Tsurimoto, Toshiki et al., "Stable Expression and Replication of Hepatitis B Virus Genome . . . ," *Proc. Natl. Acad. Sci. USA*, 84:444–448 (1987).

Vargha, L., "Uber die Substitution von Tosyloxy–Gruppen Durch Acetoxy–Gruppen in Polyoxy–Verbindugen. Eine neue Darstellungsweise von 1–ldose–Derivaten aus d–Glucose," *Chem. Ber.*, 87(9):1351–1357 (1954).

Volk, Wesley A., editor, "Hepatitis," *Essentials of Medical Microbiology, J. B. Lippincott Company, (Philadelphia/Toronto), 2nd Ed., pp. 609–618 (1982)*.

Vorbrüggen, et al., "Nucleoside Synthesis with Trimethylsllyl Triflate and Perchlorate as Catalysts," *Chem. Ber.*, 114:1234–1255 (1981). Wilson, L. J., et al., "The Synthesis and Anti–HIV Activity of Pyrimidine Dioxolanyl Nucleosides," *Bloorganic & Medicinal Chemistry Letters,* 3(2):169–147 (1993).

Wilson, L. J., et al., "A General Method for Controlling Glycosylation Stereochemistry in the Synthesis . . . ," *Tetrahedron Lett.*, 31(13):1815–1818 (1990).

World Health Organization, "Progress in the Control of Viral Hepatitis: Memorandum from a WHO Meeting," *Bulletin of the World Health Organization, 66(4):443–455 (1988)*.

Yokota et al., "Comparative Activities of Several Nucleoside Analogs Against Duck . . . ," *Antimicrobial Agents and Chemotherapy*, 34(7):1326–1330 (1990).

Zhu, Zhou, et al., "Cellular Metabolism of 3'–Azido-2', 3'–Dideoxyuridine with Formation of 5'–O–Diphophoshexase . . . " *Molecular Pharmacology*, 38:929–938 (1990).

L-NUCLEOSIDES FOR THE TREATMENT OF HEPATITIS B-VIRUS

This invention was supported in part by the United States Department of Health and Human Services under grant numbers NIH R01AI-33655 AND NCI CA44358.

This application is a continuation of U.S. Ser. No. 08/189,070, filed on Jan. 28, 1994, now pending.

This invention is in the area of methods for the treatment of hepatitis B virus (also referred to as "HBV") and Epstein-Bar Virus (referred to as "EBV") that includes administering an effective amount of one or more of the active compounds disclosed herein, or a pharmaceutically acceptable derivative or prodrug of one of these compounds.

BACKGROUND OF THE INVENTION

HBV is second only to tobacco as a cause of human cancer. The mechanism by which HBV induces cancer is unknown, although it is postulated that it may directly trigger tumor development, or indirectly trigger tumor development through chronic inflammation, cirrhosis, and cell regeneration associated with the infection.

Hepatitis B virus has reached epidemic levels worldwide. After a two, to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed. Patients typically recover from acute viral hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and Worldwide, almost 300 million carriers. Chronic persistent hepatitis can cause fatigue, cirrhosis of the liver, and hepatocellular carcinoma, a primary liver cancer.

In western industrialized countries, high risk groups for HBV infection include those in contact with HBV carriers or their blood samples. The epidemiology of HBV is in fact very similar to that of acquired immunodeficiency syndrome, which accounts for why HBV infection is common among patients with AIDS or HIV-associated infections. However, HBV is more contagious than HIV.

The Epstein-Barr virus (EBV) is a member of the genus Lymphocryptovirus, which belongs to the subfamily gammaherpesvirinae. It is notably lymphotropic. EBV has the classic structure of herpesviruses, viz., its double-stranded DNA genome is contained within an icosapentahedral nucleocapsid, which, in turn, is surrounded by a lipid envelope studded with viral glycoproteins. An amorphous tegument protein occupies the space between the envelope and the nucleocapsid.

All human herpesviruses infect and replicate within lymphocytes to some extent, but EBV does so efficiently. Most importantly, the pathogenesis and host responses to infection with EBV are more dependent upon lymphocytic infection than is evident with the other human herpesviruses.

EBV is now recognized as a cause of B-cell lymphoproliferative diseases, and has been linked to a variety of other severe and chronic illnesses, including a rare progressive mononucleosis-like syndrome and oral hairy leukoplakia in AIDS patients. The suggestion that EBV is a major cause of chronic fatigue has not withstood scrutiny.

EBV is primarily transmitted through the saliva, although some infections are transmitted by blood transfusion. More than 85% of patients in the acute phases of infectious mononucleosis secrete EBV.

EBV has been associated with cancer. At least two groups of patients are at risk for development of EBV-associated lymphomas: those who have received transplants of kidney, heart, bone marrow, liver, or thymus under the cover of immunosuppressive therapy, and patients with AIDS. EBV-associated cancers include Burkitt's Lymphoma and Nasopharyngeal Carcinoma.

In light of the fact that hepatitis B virus and Epstein-Barr virus have severe and often tragic effects on the infected patient, there remains a strong need to provide new effective pharmaceutical agents to treat humans infected with the viruses that have low toxicity to the host.

Therefore, it is an object of the present invention to provide a compound, composition, and method for the treatment of hepatitis B virus.

It is another object of the present invention to provide a compound, composition, and method for the treatment of Epstein Barr virus.

SUMMARY OF THE INVENTION

A method for the treatment of a host, and in particular, a human, infected with HBV or EBV is provided that includes administering an HBV- or EBV-treatment amount of an L-nucleoside of the formula:

wherein R is a purine or pyrimidine base. In a preferred embodiment, the nucleoside is provided as the indicated enantiomer and substantially in the absence of its corresponding enantiomer (i.e., in enantiomerically enriched or enantiomerically pure form).

In one preferred embodiment, the active compound is 2'-fluoro-5-methyl-β-L-arabinofuranosyluridine (also referred to as L-FMAU). This compound is a potent antiviral agent against HBV and EBV and exhibits low cytotoxicity. Other specific examples of active compounds include $N_1$-(2'-deoxy-2'-fluoro-β-L-arabinofuranosyl)-5-ethyluracil, $N_1$-(2'-deoxy-2'-fluoro-β-L-arabinofuranosyl)-5-iodocytosine), and $N_1$-(2'-deoxy-2'-fluoro-β-L-arabinofuranosyl)-5-iodouracil.

Figure 1:
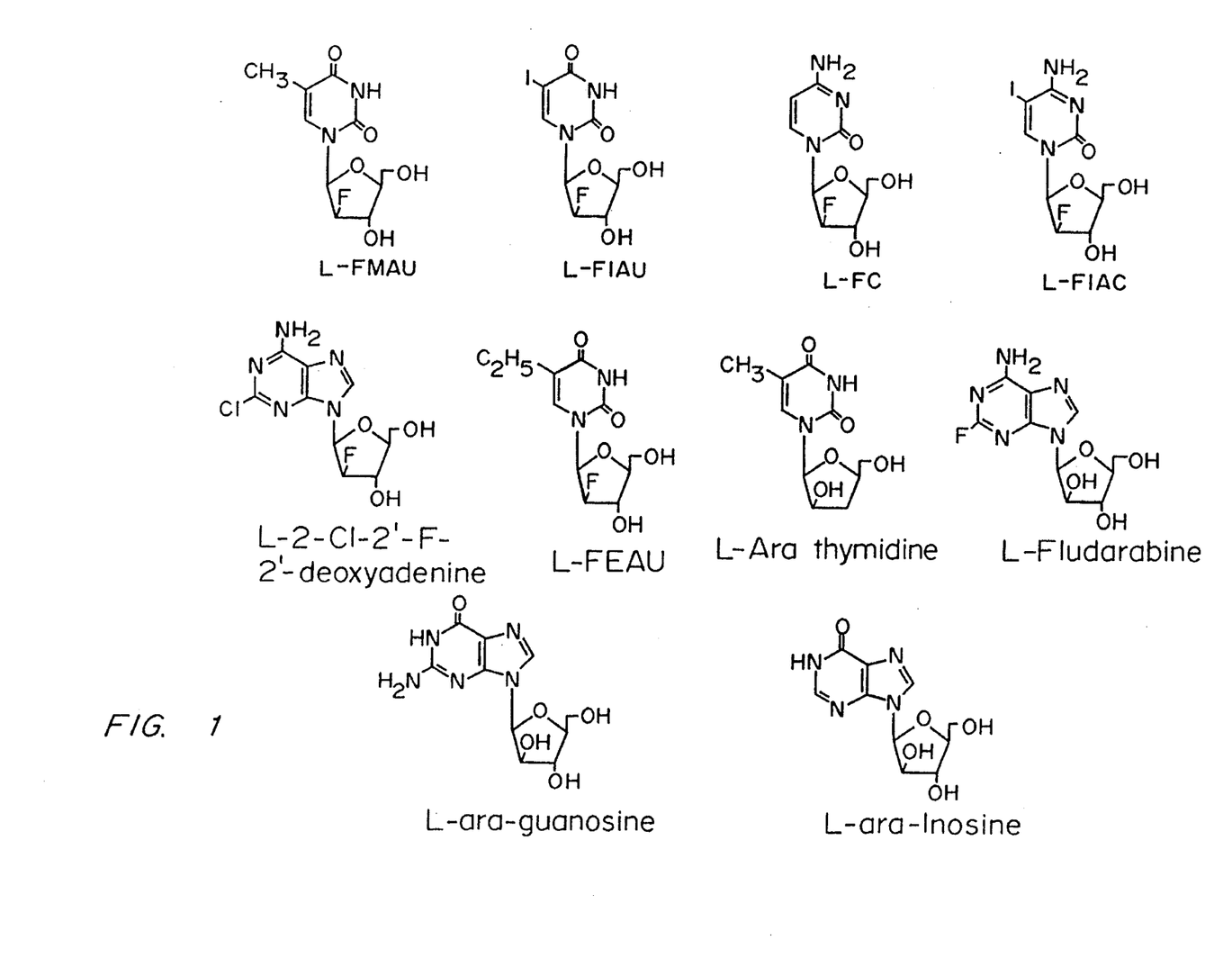
FIG. 1 is an illustration of selected L-nucleosides that fall within the present invention: L-FMAU (2'-fluoro-5-methyl-β-L-arabinofuranosyluridine), L-FIAU (2'-fluoro-5-iodo-β-L-arabinofuranosyluridine), L-FC (2'-fluoro-β-L-arabinofuranosylcytosine), L-FIAC (2'-fluoro-5-iodo-β-L-arabinofuranosylcytosine), L-2-Cl-2'-F-2'-deoxyadenine, L-FEAU (2'-fluoro-5-ethyl-β-L-iarabinofuranosyluridine), L-arathymidine, L-fludarabine, L-araguanosine, and L-arainosine.
Figure 2:
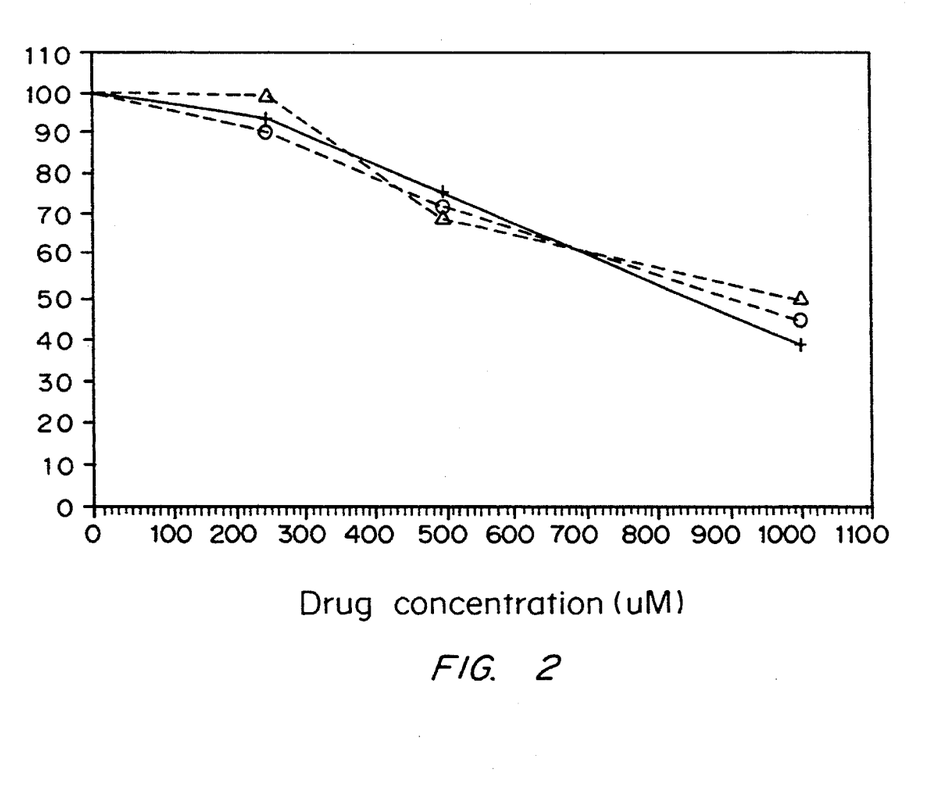
FIG. 2 is a graph of the percentage of viable cells versus drug concentration of L-FMAU in H1 cells.

In an alternative embodiment, an L-nucleoside is provided for use in the treatment of HBV or EBV that contains a 2'-arabino-hydroxyl group, for example, L-arathymidine, L-fludarabine, L-ara-guanosine, and L-ara-inosine, as illustrated in FIG. 1.

The L-nucleosides disclosed herein and their pharmaceutically acceptable derivatives or pharmaceutically acceptable formulations containing these compounds are useful in the prevention and treatment of HBV infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue. The compounds can likewise be used in the treatment of EBV-associated disorders. These compounds or formulations can also be used prophylactically to prevent or retard the progression of clinical illness in individuals who are anti-HBV or anti-EBV atibody or HBV- or EBV-antigen positive or who have been exposed

DETAILED DESCRIPTION OF THE INVENTION

As used herein, the term "enantiomerically pure" refers to a nucleoside composition that includes at least approximately 95%, and preferably approximately 97%, 98%, 99%, or 100% of a single enantiomer of that nucleoside.

As used herein, the term alkyl specifically includes but is not limited to $C_1$ to $C_{10}$ methyl, ethyl, propyl, butyl, pentyl, hexyl, isopropyl, isobutyl, sec-butyl, t-butyl, isopentyl, amyl, t-pentyl, cyclopentyl, and cyclohexyl.

As used herein, the term acyl specifically includes but is not limited to acetyl, propionyl, butyryl, pentanoyl, 3-methylbutyryl, hydrogen succinate, 3-chlorobenzoate, benzoyl, acetyl, pivaloyl, mesylate, propionyl, valeryl, caproic, caprylic, capric, lauric, myristic, palmitic, stearic, and oleic.

As used herein, and unless otherwise defined, the term aryl refers to phenyl.

The term "protected" as used herein and unless otherwise defined refers to a group that is added to an oxygen or nitrogen atom to prevent its further reaction during the course of derivatization of other moieties in the molecule in which the oxygen or nitrogen is located. A wide variety of oxygen and nitrogen protecting groups are known to those skilled in the art of organic synthesis.

The term purine or pyrimidine base includes, but is not limited to, adenine, $N^6$-alkylpurines, $N^6$-acylpurines (wherein acyl is C(O) (alkyl, aryl, alkaryl, or aralkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, $N^6$-thioalkyl purine, 5-azacytidinyl, 5-azauracilyl, triazolopyridinyl, imidazolopyridinyl, pyrrolopyrimidinyl, pyrazolopyrimidinyl. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, tritylmethyl, alkyl groups, acyl groups such as acetyl, propionyl, butyl, methylsulfonyl, and p-toluylsulfonyl. It specifically includes 5-methyl uracil (thymine), 5-iodouracil, cytosine, and 5-ethyluracil.

The invention as disclosed herein is a method and composition for the treatment of HBV infection, EBV infection, and other viruses replicating in a like manner, in humans or other host animals, that includes administering an effective amount of one or more of the above-identified L-nucleosides, or a physiologically acceptable derivative, or a physiologically acceptable salt thereof, optionally in a pharmaceutically acceptable carrier. The compounds of this invention either possess anti-HBV activity, anti-EBV-activity, or are metabolized to a compound or compounds that exhibit anti-HBV or anti-EBV activity. The compounds disclosed herein can also be used to treat HBV and EBV associated disorders.

The active compound can be administered as any derivative that upon administration to the recipient, is capable of providing directly or indirectly, the parent compound, or that exhibits activity itself. Nonlimiting examples are the pharmaceutically acceptable salts (alternatively referred to as "physiologically acceptable salts"), and the 5' and purine or pyrimidine acylated or alkylated derivatives of the active compound (alternatively referred to as "physiologically active derivatives"). In one embodiment, the acyl group is a carboxylic acid ester in which the non-carbonyl moiety of the ester group is selected from straight, branched, or cyclic alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The alkyl group can be straight, branched, or cyclic, and is optimally a $C_1$ to $C_{18}$ group.

I. Synthesis of L-Nuclieosides

The L-nucleosiides disclosed herein can be prepared as described in detail below, or by other assays known to those skilled in the art.

Figure 3:
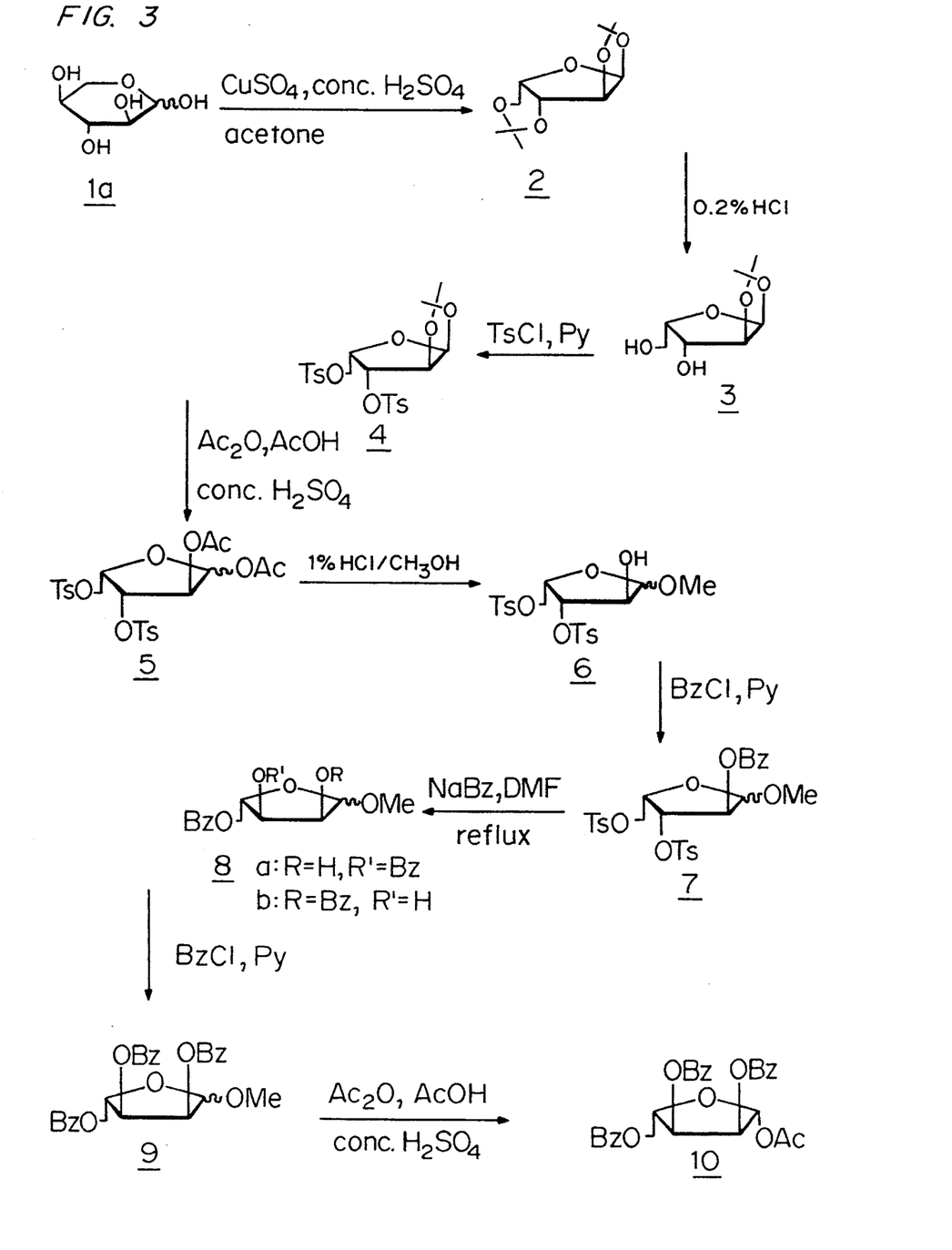
FIG. 3 is a schematic illustration of the preparation of 1-O-acetyl-2,3,5-tri-O-benzoyl-β-L-ribofuranose (compound 10).
Figure 4:
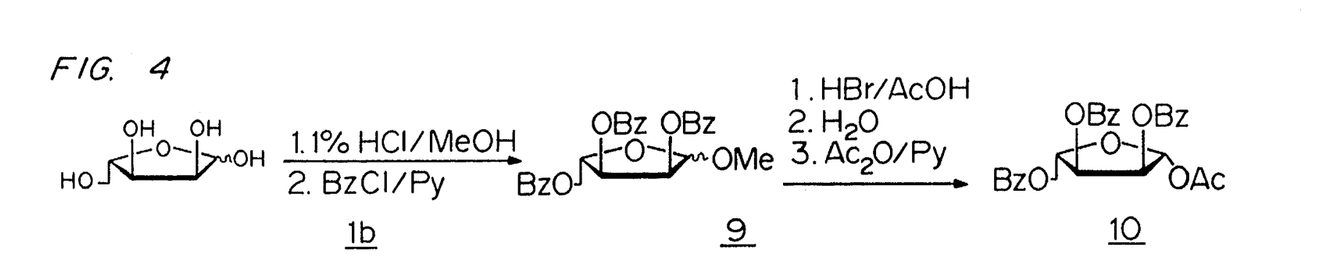
FIG. 4 is a schematic illustration of an alternative preparation of 1-O-acetyl-2,3,5-tri-O-benzoyl-β-L-ribofuranose (compound 10).
Figure 5:
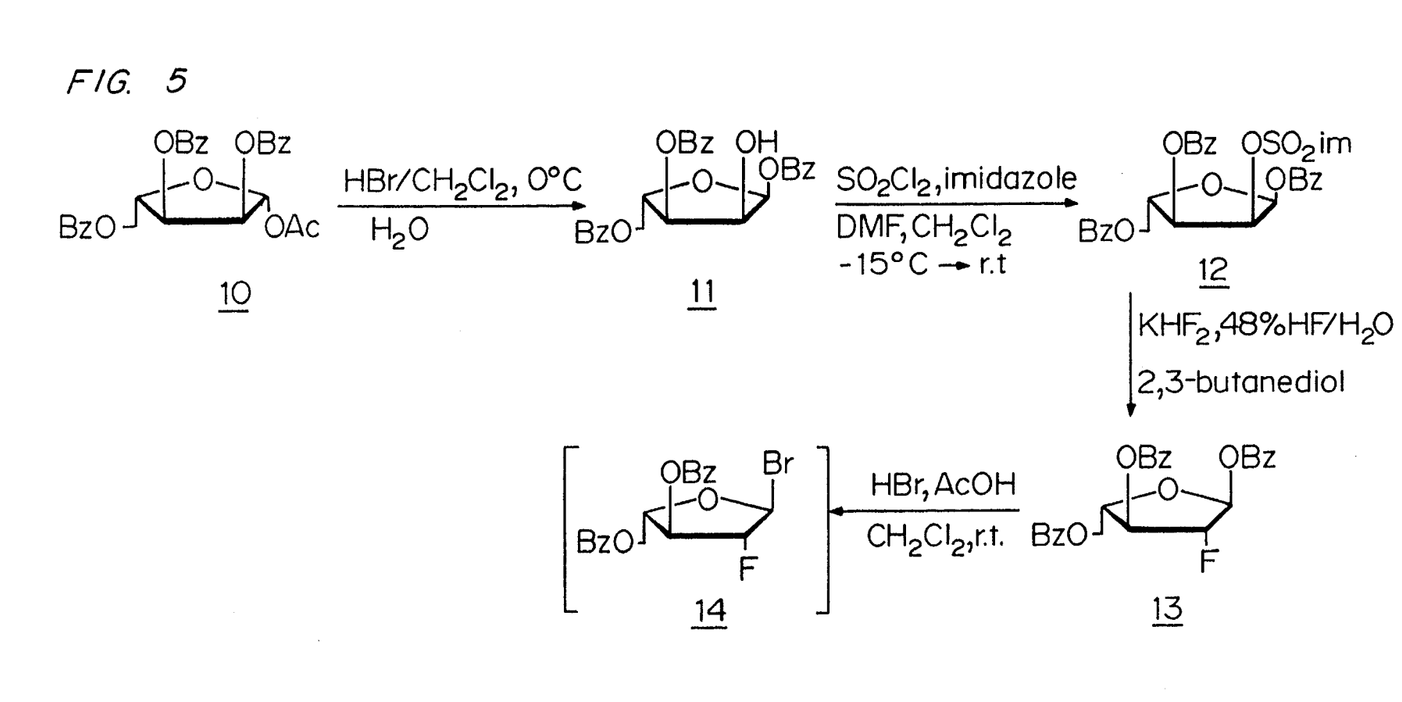
FIG. 5 is a schematic illustration of a method for the preparation of 1,3,5-tri-O-benzoyl-2-deoxy-2-fluoro-α-L-arabinofuranose (compound 13).
Figure 6:
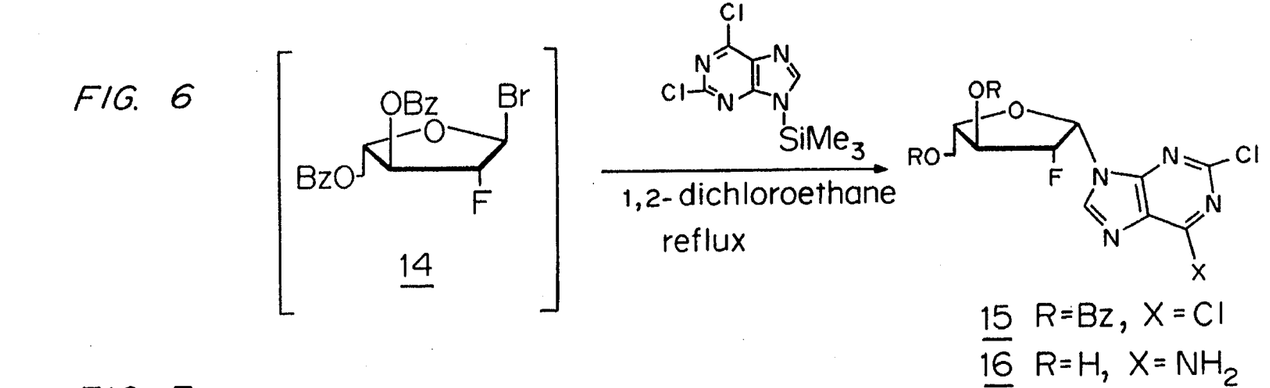
FIG. 6 is schematic illustration of a method for the preparation of $N_9$-[3',5'-di-O-benzoyl-2'-deoxy-2'-fluoro-β-L-arabinofuranosyl]-2,6-d-chloropurine (compound 15) and $N_9$-[2'-deoxy-2'-fluoro-β-L-arabinofuranosyl]-2,6-di-chloropurine (compound 16).
Figure 7:
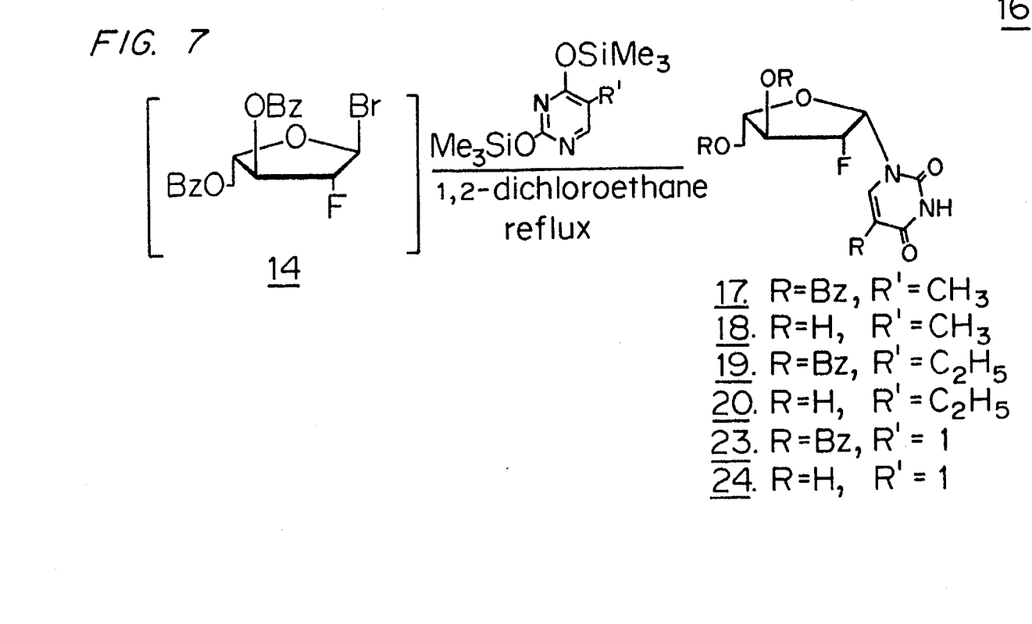
FIG. 7 is an illustration of a method for the preparation of a number of 2'-deoxy-2'-fluoro-β-L-arabinofuranosyl -pyrimidines (compounds 17–24).
Figure 8:
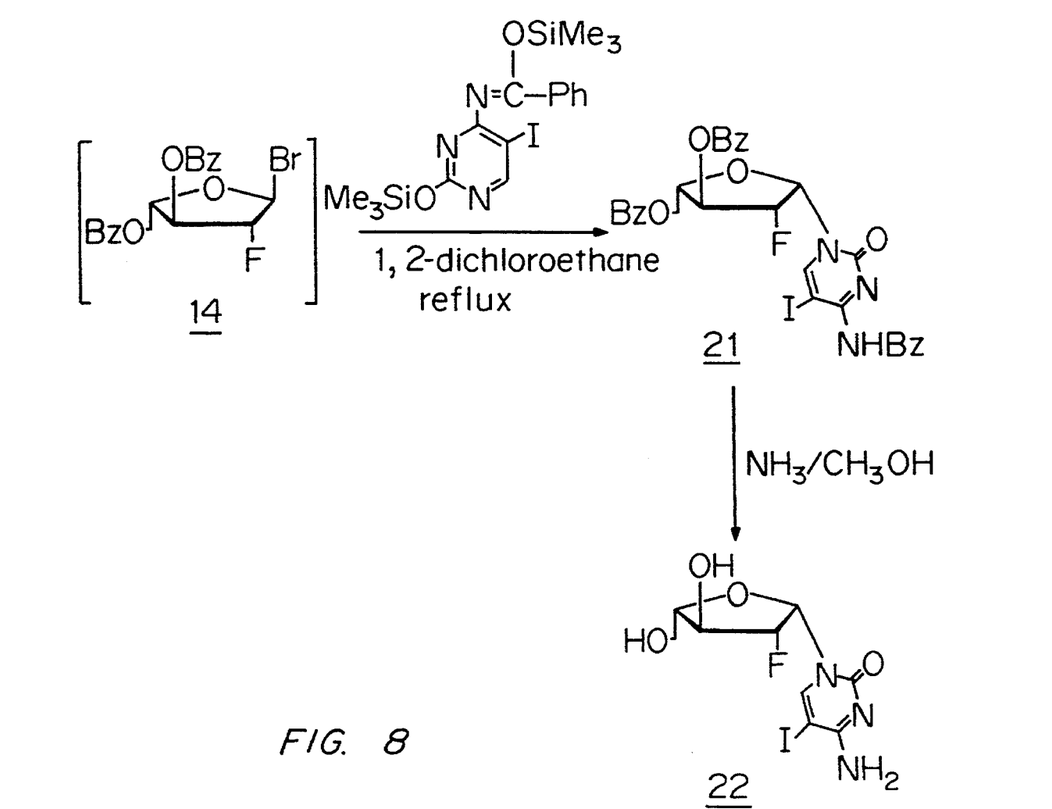
FIG. 8 is an illustration of a method for the preparation of $N_1$-(2'-deoxy-2'-fluoro-β-L-arabinofuranosyl)-5-iodocytosine) (compound 22).

Referring to FIG. 3, starting from L-xylose (1a), the key intermediate 1-O-acetyl-2,3,5-tri-O-benzoyl-β-L-ribofuranose (10) was synthesized in a total yield of 20% (L. Vargha, *Chem. Ber.*, 1954, 87, 1351; Holy, A., et al., *Synthetic Procedures in Nucleic Acid Chemistry*, V1, 163–67). As shown in FIG. 4, compound 10 can also be synthesized from the more expensive starting material L-ribose (Holy, A., et al., *Synthetic Procedures in Nucleic Acid Chemistry*, V1, 163–67). FIG. 3 illustrates an alternative synthesis of compound 10 (yield of 53%), which was subsequently fluorinated at $C_2$ (*J. Org. Chem.* 1985, 50, 3644–47) to obtain 1,3,5-tri-O-benzoyl-2-deoxy-2-fluoro-L-arabinofuranosie (13), which was condensed with different bases through the bromosugar to provide the 2'-deoxy-2'-fluoroarabinofuranosyl nucleosides in various yields.

1,2-Di-O-isopropylidene-α-L-xylofuranose (3)

To 650 ml of anhydrous acetone was added 4 ml of conc. sulfuric acid, 5 g of molecular sieve (4A), 80 g of anhydrous cupric sulfate and 50 g of L-xylose and the mixture was stirred at room temperature for 36 hours. The reaction mixture was filtered and washed thoroughly with acetone, the combined filtrate was neutralized with ammonium hydroxide then evaporated to dryness. Ethyl acetate (200 ml) was added, then filtered and evaporated, yielded an oil which was dissolved in 250 ml of 0.2% HCl solution and stirred at room temperature for 2.5 hours. The pH was adjusted to 8 with sat. $NaHCO_3$, then evaporated to dryness, the residue was extracted with ethyl acetate. Removal of the solvent provided a yellow oil of compound 3 (41.7 g, 82.3%).

$^1$H-NMR($CDCl_3$): δ5.979 (d, J=3.78 Hz,1H, H-1); 4.519(d, J=3.6 Hz, 1H, H-2);4.308(bd, 1H, H-3); 4.080(m, 3H, H-4 and H-5); 1.321(s, 3H, $CH_3$); 1.253 (s, 3H, $CH_3$).

1,2-Di-O-isopopylidene-3,5-di-O-o-tolylsulfonyl-α-L-xylofuranose (4)

Compound 3 (40 g, 210 mmol) was stirred in 500 ml of anhydrous pyridine at 0° C., while TSCl (75 g, 393 mmol) was dissolved in 100 ml of $CHCl_3$ was added dropwise. After 3 hours, another portion of TsCl (50 g, 262 mmol) in 50 ml of $CHCl_3$ was added the same as above. The mixture was stirred at r.t. for 24 hrs, then chilled at 0° C., water (10 ml) was added, then stirred at r.t. for 30 minutes. The reaction mixture was poured into 500 ml of ice-water, extracted with $CHCl_3$ (150 ml×4), washed with 1.5M $H_2SO_4$ (150 ml×4), sat.$NaHO_3$ (200 ml×2), dried ($MgSO_4$). Removing solvent gave a brown syrup, which upon crystallization from EtOH, gave 4 as a white solid (103.8g, 99%).

$^1$H-NMR ($CDCl_3$): δ7.282, 7.836 (m, 8H, OTs); 5.849 (d, J=3.51 Hz, 1H, H-1); 4.661, 4.779 (m, 2H, H-3 and H-4); 4.193(dd, 1H, H-2); 4.011 (d, 2H, H-5); 2.448, 2.478 (2s, 6H, -OTs); 1.261, 1.320 (2s, 6H, $CH_3$).

1,2-Di-O-acetyl-3,5-di-O-p-tolylsulfonyl-α,β-xylofuranose (5)

Compound 4(70 g,140.5 mmol) was dissolved in 700 ml of glacial AcOH and 100 ml of $Ac_2O$ while 50 ml of conc. sulfuric acid was added dropwise at 0° C. The resulting solution was stirred at r.t overnight and then poured into 1 L of ice-water, extracted with $CHCl_3$ (200 ml×4), washed with sat. $NaHCO_3$, dried ($MgSO_4$). After removing solvent in vacuo, gave 5 as a syrup (84.2 g, crude yield 110%).

Methyl-3,5-di-O-p-tolylsulfonyl-α,β-xylofuranose (6)

The crude 5 (80 g) was stirred. in 500 ml of 1% HCl/$CH_3OH$ at r.t. for 30 hrs. The solvent was removed under reduced pressure, the residue dissolved in 300 ml of $CHCl_3$, washed with sat. $NaHCO_3$, dried ($MgSO_4$). Removing solvent gave 6 as a syrup (60 g, 90% from 4).

Methyl-2-O-benzoyl-3,5-di-O-p-tolylsulfonyl-α,β-xylofuranoside (7)

The syrup 6 (60 g, 127 mmol) was dissolved in 200 ml of pyridine and stirred at 0° C., while benzoyl chloride (40 ml, 345 mmol) was added dropwise, the resulting solution was stirred at r.t. for 17 hrs. It was concentrated to about 50 ml, then poured into 300 ml of ice-water, extracted with $CHCl_3$, washed with 3N $H_2SO_4$ and sat. $NaHCO_3$, dried ($MgSO_4$). After evaporation of the solvent, gave 7 as a syrup (71 g, 97%).

Methyl-2,3,5-tri-O-benzoyl-α-β-L-ribofuranoside (9)

The syrup 7 (70 g) and sodium benzoate (100 g, 694 mmol) were suspended in 1200 ml of DMF and mechanically stirred under reflux for 16 hrs. It was cooled to r.t. and then poured into 1 L of ice-water, extracted with ether, dried ($MgSO_4$). Evaporation of solvent gave a syrup (50 g, 8a and 8b), which was dissolved in 180 ml of pyridine and benzoylated (BzCl, 20 ml, 172 mmol) for 17 hrs at r.t. After work up, gave 9 as a brown syrup (48 g, 83% from 7).

1-O-acetyl-2,3,5-tri-O-benzoyl-β-L-ribofuranose (10)

Compound 9 (26 g, 54.6 mmol) was treated with 275 ml of glacial acetic acid, 55 ml of acetic anhydride and 16 ml of conc. sulfuric acid at 0° C. to r.t. for 17 hrs. Then poured into 1 L of ice-water, extracted with chloroform (200 ml×4). The combined extract was washed with sat. $NaHCO_3$ and dried ($MgSO_4$). Removing solvent gave a brown syrup which was treated with ethanol to give 10 as a white solid. (8.8 g, 32%). m.p.124.7° C., lit. 129°–130° C.; D from: 130°–131° C. $[α]_D$=−45.613 (c 1.0, $CHCl_3$), D form: $[α]_D$= +44.2.

$^1$H-NMR($CDCl_3$): δ7.317, 8.134 (m, 15H, OBz); 6.437 (s, 1H, H-1); 5.835 (m, 2H, H-2 and H-3); 4,649 (m, 3H, H-4 and H-5); 2.003 (s, 3H, $\underline{CH_3}$COO—).

1-O-acetyl-2,3,5-tri-O-benzoyl-β-L-ribofuranose (from L-ribose)

L-Ribose (5 g, 33.3 mmol) was suspended in 120 ml of 1% HCl/MeOH and stirred at r.t. for 3 hrs, when a clear solution was obtained. The reaction was quenched by adding 30 ml of anhydrous pyridine, then evaporated under reduced pressure. The resulting syrup was coevaporated with pyridine (30 ml×2), then dissolved in 80 ml of anhydrous pyridine, and stirred at 0° C. while benzoyl chloride (20 ml, 172 mmol was added dropwise. After stirring at r.t. for 17 hrs, the reaction was complete. Water (10 ml) was added and the mixture was stirred at r.t. for 0.5 hr, then concentrated to about 50 ml, poured into 150 ml of ice-water, extracted with chloroform (50 ml×4), washed successively with 3N $H_2SO_4$ (30 ml×2), sat. $NaHCO_3$ (30 ml×3), dried ($MgSO_4$). Removing solvent gave 9 as a syrup of 13 g.

The crude 9 was dissolved in 80 ml of HBr/AcOH (45%, w/v) and stirred at r.t. for 1.5 hrs. To this mixture, was added glacial acetic acid (50 ml) and the resulting solution stirred at 0° C., while 34 ml of water was added slowly to keep the temperature below 7° C., then it was stirred at r.t. for 1 hr, poured into 200 ml of ice-water, extracted with chloroform (50 ml×5), the combined extracts were rewashed with sat. $NaHCO_3$, dried ($MgSO_4$). Removing solvent gave a syrup (13 g), which was dissolved in 40 ml of anhydrous pyridine, stirred at 0° C., when acetic anhydride (14 ml, 148.4 mmol) was added dropwise. After the reaction completed, it was poured into 150 ml of ice-water, extracted with chloroform (50 ml×4), washed successively with 3N $H_2SO_4$ (30 ml×2), sat. $NaHCO_3$ (50 ml×2), dried ($MgSO_4$). Removing solvent and treating with methanol, gave 10 as a white solid (9.2 g, 53.7% from L-ribose).

1,3,5-Tri-O-benzoyl-α-L-ribofuranose (11)

Compound 10 (9 g, 17.84 mmol) was stirred in 100 ml of $CH_2Cl_2$ at 0° C. while 70 ml of $CH_2Cl_2$ containing HBr (3.2 g, 30.5 mmol) was added in one portion. The mixture was stirred at 0° C. for 3.5 hrs, water (55 ml) was added and the mixture stirred at r.t. for 18 hrs. The organic layer was separated, washed with sat. $NaHCO_3$, dried ($MgSO_4$). After evaporation of the solvent, a foam was obtained, which upon recrystallization from CH$_2$Cl$_2$ and n-hexane, gave 11 as a white solid. (6.2 g, 75.5%). m.p. 137°–138° C., lit. 140°–141° C., [α]$_D$=−81.960 (c 0.55, CHCl$_3$; D form: [α]$_D$=+83.71.

$^1$H-NMR (CDCl$_3$): δ7.312, 8.187 (m, 15H, OBz); 6.691 (d, J=4.59 Hz, H-1); 5.593 (dd, J$_{4-3}$=6.66 Hz; J$_{2-3}$=1.8 Hz, 1H, H-30; 4.637, 4.796 (m, 4H, H-2, H-4 and H-5); 2.3 (b, OH).

1,3,5-Tri-O-benzoyl-2-O-imidazosulfuryl-α-L-ribofuranose (12)

Compound 11 l5.94 g, 12.84 mmol) was stirred in 50 ml of anhydrous CH$_2$Cl$_2$ at −15° C. (dry ice-CCl$_4$). Anhydrous DMF (15 ml) and sulfuryl chloride (3.2 ml, 3.98 mmol) was added sequentially. The solution was stirred at −15° C. for 30 minutes then left at r.t. for 4 hrs. Imidazole (8.7 g, 12.78 mmol) was added in three portions while the reaction mixture was cooled in an ice bath, then it was stirred at r.t. for 17 hrs. The mixture was poured into 150 ml of ice-water and the water phase extracted with CH$_2$Cl$_2$ (50 ml×3). The combined organic layer was washed with water, dried (MgSO$_4$). After purification on column (Hexane:EtOAc/ 5:1–1:1) gave 12 as a white solid (3.7 g, 49%). m.p. 124.5°–125.5° C., lit: 129° C.; [α]$_D$=−68.976; D form: +66.154.

$^1$H-NMR(CDCl$_3$): δ6.9, 8.2 (m, 18H, Ar—H); 6.67 (d, J=4.4 Hz, 1H, H-1); 5.59 (dd, 1H, H-3), 5.21 (dd, 1H, H-2); 4.5, 4.8 (m, 3H, H-4 and H-5).

1,3,5-Tri-O-benzoyl-2-deoxy-2-fluoro-α-L-arabinofuranose (13).

A suspension of 12 (3.33 g, 5.62 mmol), KHF$_2$ (1.76 g, 22.56 mmol) in 30 ml of 2,3-butanediol was stirred under argon. It was heated to 150° C. while 1 ml of HF/H$_2$O (48%, 27.6 mmol) was added and the mixture was stirred at 160° C. for 1.5 hrs. Brine-ice was added to quench the reaction, then extracted with methylene chloride (50ml×4), the combined extract was washed with brine, water, sat. NaHCO$_3$, dried over anhydrous magnesium sulfate and activated carbon (Darco-60). It was poured on a silica gel pad (5cm× 5cm), washed with methylene chloride and then EtOAc, to give a syrup which from 95% EtOH,13 (1.3 g, 49.8%) was crystallized. m.p. 77°–78° C.; lit.: 82° C.

$^1$H-NMR(CDCl$_3$): δ7.314, 8.146 (m, 15H, OBz); 6.757 (d, J=9.1 Hz, 1H, H-1); 5.38 (d, J=48.5 Hz, 1H, H-2); 5.630 (dd, J=22.5 Hz, 1H, H-3); 4.768 (m, 3H, H-4 and H-5).

N$_9$-[3',5'-Di-O-benzoyl-2'-deoxy-2'-fluoro-β-L-arabinofuranosyl]-2,6-di-chloro-purine (15)

Compound 13 (464 mg, 1 mmol) was dissolved in 10 ml of methylene chloride while 1.4 ml of HBr/AcOH (45% w/v) was added. The solution was stirred at r.t. for 24 hrs, then evaporated to dryness, the residue was dissolved in 20 ml of methylene chloride, washed with water, sat. NaHCO$_3$, dried (MgSO$_4$). Filtration and evaporation gave the bromosugar 14 (100%, based on TLC).

At the same time, 2,6-Di-chloro-purine (378 mg, 2 mmol) was suspended in 15 ml of HMDS and 2 mg of ammonium sulfate, and refluxed for 2 hrs. The HMDS was evaporated with high vacuum under N$_2$ to give the white silylated base.

The bromosugar 14 was dissolved in 25 ml of anhydrous 1,2-dichloroethane. The resulting solution was added to the silylated base under N$_2$. The mixture was stirred under reflux for 2 days. Chloroform (30 ml) was added, then washed successively with water (20 ml×2), sat. NaHCO$_3$(20 ml×2), sat. NaCl solution (20 ml×2), dried (MgSO$_4$). From CHCl$_3$, 15 (105 mg, 19.7%) was crystallized. m.p. 158° C.; D form: 158° C. UV(Methanol): λ$_{max}$: 238.50 nm, 273.0 nm.

$^1$H-NMR (300 MHZ, DMSO-d$_6$): δ8.82 (d, J=1.5 Hz, 1H, H-8); 7.49, 8.33 (m, 10H, OBz,); 6,767 (dd, J$_{H-H}$=4 Hz, K$_{F-H}$=13.8 Hz, 1H, H-1'); 5.854 (dq, J=67.4 Hz, 1H, H-2'); 5.910 (m, 1H, H-3'); 4.751 (m, 3H, H-4' and H-5').

N$_9$[2'-deoxy-2'-fluoro-β-L-arabinofuranosyl]-2,6-dichloropurine (16)

Compound 15 (70 mg, 0.13 mmol) was dissolved in 25 ml of sat. NH$_3$/CH$_3$OH in a sealed steel bomb and heated at 90° C. for 6 hrs. Removing solvent Under reduced pressure gave a yellow semisolid which was purified by preparative TLC (9:1/CHCl$_3$:CH$_3$OH). Lyophilization from water and 1,4-dioxane gave a white powder 16 (30 mg, 75%). UV(H$_2$O) pH2, λ$_{max}$ 212.00 nm, 263.50 nm (ε6711); pH7, λ$_{max}$ 213.50 nm, 263.00 nm (ε7590); pH11, λmax 213.5 nm, 263.00 nm (ε5468).

$^1$H-NMR (300 MHz, DMSO-d$_6$): δ8.279 (d, J=1.5 Hz, 1H, H-8); 7.908 (bs, 2H, NH$_2$); 6.321 (dd, J$_{H-H}$=4.4 Hz, J$_{F-H}$=13.8 Hz, 1H, H-1'); 5.986 (t, 1H, 5'—OH); 5.230 (dt, J$_{F-H}$=52.6 Hz, 1H, H-2'); 5.115 (d, 1H, 3'—OH); 4.425 (dq, J$_{F-H}$=19 Hz, 1H, H=3'); 3.841 (m, 1H, H-4'); 3,636 (d, 2H, H-5').

N$_1$-(2'-Deoxy-2'-fluoro-3',5'-di-O-benzyl-β-L-arabinofuranosyl)-thymine (17)

To a solution of 13 (400 mg, 0.86 mmol) in anhydrous CH$_2$Cl$_2$ (10 ml) was added hydrogen bromide in acetic acid (45% w/v, 1.5 ml), and the resulting solution was stirred at r.t. for 17 hrs. After evaporation of the solvent and coevaporation with toluene, 14 was obtained.

At the same time, thymine (215 mg, 1.72 mmol) was refluxed in HMDS (25 ml) under nitrogen for 17 hrs, to get a homogeneous solution. After evaporation of the solvent, gave a silylated thymine.

A solution of 14 in dichloroethane (50 ml) was added to the silylated thymine and the resulting solution was refluxed under nitrogen for 3 days. Water was added and then extracted with CHCl$_3$. The organic layer was washed with water, brine and dried (MgSO$_4$). Evaporation of the solvent gave the crude product, which was purified on preparative TLC using 2% MeOH/CHCl$_3$ to give 17 (235 mg, 58%). m.p. 99°–101° C. UV(Methanol): 230, 264 nm [α]$_D$=+ 22.397.

$^1$H-NMR(CDCl$_3$): δ7.343–8.389 (m, 12H, Ar—H, NH); 6.34 (dd, J$_{H-H}$=2.97 Hz, J$_{F-H}$=28.32 Hz, 1H, H-1'); 5.383 (dd, J$_{H-H}$=2.7 Hz, J$_{F-H}$=63.27 Hz, 1H, H-2'); 5.565 (dd, 1H, H-3'); 4.812 (d, 2H, H-5'); 4.466 (m, 1H, H-4'); 1.775 (s, 3H, CH$_3$). Anal. (C$_{24}$H$_{21}$N$_2$O$_7$F), C: 61.01; H, 4.57; N: 5.73; F: 3.92. N$_1$-(2'-Deoxy-2'-fluoro-β-L-arabinofuranosyl)-thymine (18)

Compound 17 (145 mg, 0.309 mmol) was treated with NH$_3$/CH$_3$OH at r.t. for 18 hrs. After evaporation of the solvent and purified on preparative TLC (15% MeOH/ CHCl$_3$, 18 (70 mg, 87.5%) was obtained. m.p. 174°–175° C. UV: 264 nm, [α]$_D$=−104.36.

H-NMR (DMSO-d$_6$): δ11.401 (s, 1H, NH); 7.575 (s, 1H, H-6); 6.093 (dd, J$_{H-H}$=4.41 Hz, J$_{F-H}$=15.6 Hz, 1H, H-1'); 5.844 (d, 1H, 3'—OH); 5.019 (dt, J$_{F-H}$=53.3 Hz, 1H, H-2'); 5.087 (t, 1H, 5'—OH); 4.194 (dq, 1H, H-3'); 3.647 (m, 3H, H-4' and H-5'); 1.781 (s, 3H, CH$_3$). Anal. (C$_{10}$H$_{13}$N$_2$FO$_5$), C: 44.80; H: 4.97; N: 10.04; F: 7.03.

N$_1$-(2'-Deoxy-2'-fluoro-3',5'-di-O-benzoyl-β-L-arabinofuranosyl)-5-ethyluracil (19)

To a solution of 13 in anhydrous dichloromethane (10 ml) was added hydrogen bromide in acetic acid (45% w/v, 0.97 ml, 5.385 mmol). The solution was stirred at r.t. for 18 hrs, after evaporation of the solvent and coevaporation with toluene, 14 was obtained.

At the same time, 5-ethyluracil (0.75 g, 5.39 mmol) was suspended in HMDS (10 ml) with ammonium sulfate (5 mg) and refluxed for 5 hrs. under nitrogen to give a homogeneous solution.

The silylated base solution was evaporated to dryness with avoiding the contact of moisture. To the obtained syrup was added a solution of 14 in anhydrous 1,2-dichloroethane (10 ml). The reaction mixture was stirred at 95° C. under nitrogen for 20 hrs, then evaporated under vacuum to dryness to give a yellow solid, which was mixed with 5 ml of $CH_3OH/CHCl_3$ (1:1) and filtered. The filtrate was evaporated to give a residue, which was chromatographed on silica gel column ($CH_3OH/CHCl_3$, 0–1%) to give a white solid 19 (0.557 g, 100%).

$^1$H-NMR (DMSO-$d_6$): δ11.55 (s, 1H, NH); 7.51, 8.08 (m, 10H, Ar—H); 7.32 (s, 1H, H-6); 6.29, 6.37 (dd, $J_{H-H}$=3.7 Hz, $J_{F-H}$=20 Hz, 1H, H-1'); 5.68–5.75 (dd, $J_{F-H}$=20 Hz, 1H, H-3'), 5.47–5.65 (dd, $J_{F-H}$=54 Hz, 1H, H-2'); 4.62–4.83 (m, 3H, H-4' and H-5'); 2.01, 2.09 (q, 2H, $\underline{CH_2}$—$CH_3$); 0.85 (t, 3H, $CH_3$).

$N_1$-(2'-Deoxy-2'-fluoro-β-L-arabinofuranosyl)-5-ethyluracil (20)

Compound 19 (500 mg) was dissolved in methanolic ammonia (50 ml) and stirred at r.t. for 44 hrs. The solution was evaporated to dryness to give a white solid (0.4 g), which was chromatographed on silica gel column. ($CH3OH/CHCl3$, 0–5%) to give a white solid 20 (240 mg, 84%). m.p. 158°–161° C. UV(MeOH): $\lambda_{max}$ 260 nm.

$^1$H-NMR (DMSO-$d_6$): δ11.42 (s, 1H, NH); 7.57 (s, 1H, H-6'); 6.10, 6.17 (dd, $J_{H-H}$=5.0 Hz, $J_{F-H}$=14 Hz, 1H, H-1'); 5.88 (bs, 1H, 3'—OH); 5.14, 5.19 (m, 2H, H-2' and 5'—OH); 4.98 (t, 1H, H-3'); 4.22, 4.28 (m, 1H, H-4'); 3.55, 3.78 (m, 2H, H-5') Anal. ($C_{11}H_{15}N_2O_5F$): C: 47.93; H: 5.56; N: 10.06; F: 6.68.

$N_1$-(2'-Deoxy-2'-fluoro-3',5'-di-O-benzoyl-β-L-arabinofuranosyl)-$N^4$-benzoyl-5-iodocytosine (21)

To a solution of 13 (150 mg, 0.323 mmol) in anhydrous methylene chloride (5 ml) was added hydrogen bromide in acetic acid (45% w/v, 0.29 ml, 1.615 mmol). The reaction mixture was stirred at r.t. for 9.5 hrs. After evaporating the solvent and coevaporating with toluene, 15 was obtained as a yellow syrup.

At the same time, $N^4$-benzoyl-5-iodocytosine (550 mg, 1.615 mmol) was suspended in HMDS (8 ml) with ammonium sulfate (3 mg) and refluxed for 5 hrs. under nitrogen to give a homogeneous solution.

The silylated base solution was evaporated to dryness with avoiding the contact of moisture. To the obtained syrup was added a solution of 14 in anhydrous 1,2-dichloroethane (10 ml). The reaction mixture was refluxed under nitrogen for 23 hrs, then evaporated to dryness to give a brown syrup, which was triturated with chloroform (30 ml). The resulting precipitate was filtered off and washed with chloroform. The filtrate and washings were combined and evaporated to give a brown syrup. The product mixture was separated by chromatography on silica gel column ($CH_3OH/CHCl_3$, 0–1%) to give a white solid 21 (100 mg, 45%).

$^1$H-NMR (CDCl$_3$): δ11.40 (bs, 1H, NH): 7.26, 8.20 (m, 17H, Ar—H, H-6 and NH); 6.36, 6.44 (dd, $J_{HH}$=2.8 Hz, $J_{F-H}$=21 Hz, 1H, H-1'); 5.62, 5.68 (dd, 1H, H-3'); 5.39, 5.56 (dd, 1H, H-2'); 4.58, 4.85 (m, 3H, H-4' and H-5').

$N_1$-(2'-Deoxy-2'-fluoro-β-L-arabinofuranosyl)-5-iodocytosine (22)

Compound 21 (100 mg, 0.27 mmol) was treated with sat. $NH_3$/MeOH (60 ml) at r.t. for 24 hrs. After silica gel column chromatography (0–10% $CH_3OH/CHCl_3$), gave 22 (35 mg, 71%) as a white solid. [α]$_D$=−65.4 (c 0.34, $CH_3OH$); UV(MeOH): $\lambda_{max}$=293 nm.

$^1$H-NMR (DMSO-$d_6$); δ8.04 (s, 1H, H-6); 6.74, 7.94 (s, 1H, NH); 6.01, 6.08 (dd, $J_{H-H}$=3.9 Hz, $J_{F-H}$=16.6 Hz, 1H, H-1'); 5.85 (d, 1H, 3'—OH); 5.17 (t, 1-H, 5'—OH); 5.08 (t, 1H, H-2'); 4.89 (t, 1H, H-3 '); 4.15–4.23 (m, 1H, H-4'); 3.63–3.79 (m, 2H, H-5').

$N_1$-(2'-Deoxy-2'-fluoro-3',5'-di-O-benzoyl-β-L-arabinofuranosyl)-5-iodouracil (23)

To a solution of 13 (260 mg, 0.56 mmol) in 10 ml of anhydrous $CH_2Cl_2$ was added HBr/AcOH (45%, w/v, 0.5 ml, 2.8 mmol). The reaction mixture was stirred at r.t. for 36 hrs, then evaporated to dryness. The residue was dissolved in 20 ml of $CH_2Cl_2$, washed with water (10 ml), sat. $NaHCO_3$ (10 ml), dried ($MgSO_4$). Filtration and evaporation gave the bromosugar 14 as a syrup.

At the same time, 5-iodouracil (270 mg, 1.12 mmol) was suspended in 10 ml of HMDS and refluxed for 36 hrs. to give a homogeneous solution it was evaporated under vacuum to dryness. To this was added a solution of 14 in anhydrous 1,2-dichloroethane, and the resulting solution was refluxed under $N_2$ for 1.5 days. $CHCl_3$ (20 ml ) was added, and the solution was washed successively with water (10 ml), brine (10 ml) and sat. $NaHCO_3$ (10 ml), dried ($MgSO_4$). Removing solvent gave a syrup which was crystallized in $CH_2Cl_2$ to give 23 as a yellow solid (237 mg, 73%). A part of this (70 mg) was recrystallized from 2-isopropanol to give a white solid (67 mg). UV(Methanol): $\lambda_{max}$ 230.0 nm, 276.0 nm.

$^1$H-NMR (CDCl$_3$): δ8.4, 7.3 (m, 12H, Ar—H); 6.29 (dd, $J_{H-H}$=2.43 Hz, $J_{F-H}$=21.6 Hz 1H H-1'); 5.377 (dd, $J_{H-H}$=2.8 Hz, $J_{F-H}$=61.3 Hz, 1H, H-2'); 5,55 (dd, 1H, H-3'); 4.865, 4.793 (d, 2H, H-5'); 4.588, 4.502 (m, 1H, H-4').

$N_1$-(2'-deoxy-2'-fluoro-β-L-arabinofuranosyl)-5-iodouracil (24)

Compound 23 (40 mg, 0.069 mmol) was dissolved in 25 ml of sat. $NH_3$/MeOH and stirred at r.t. for 24 hrs, then evaporated to dryness. The resulting syrup was purified on preparative TLC (5:1/$CHCl_3$:MeOH) to give 24 as a solid (19 mg, 74%). UV(MeOH): $\lambda_{max}$ 280.5 nm.

$^1$H-NMR (DMSO-$d_6$): δ11.82 (bs, CONH); 8.24 (s, 1H, H-6); 6.082 (dd, $J_{H-H}$=4.45 Hz, $J_{F-H}$=13.7 Hz, 1H, H-1'); 5.947 (d, 1H, 3'—OH); 5.296 (t, 1H, 5'—OH); 5.07 (dt, $J_{F-H}$=53 Hz, 1H, H-2'); 4.24 (bd, $J_{F-H}$=21 Hz, 1H, H-3'); 3.81, 3.55 (m, 3H, H-4', H-5').

2,3,5-Tri-O-benzyl-L-arabinose

Figure 9:
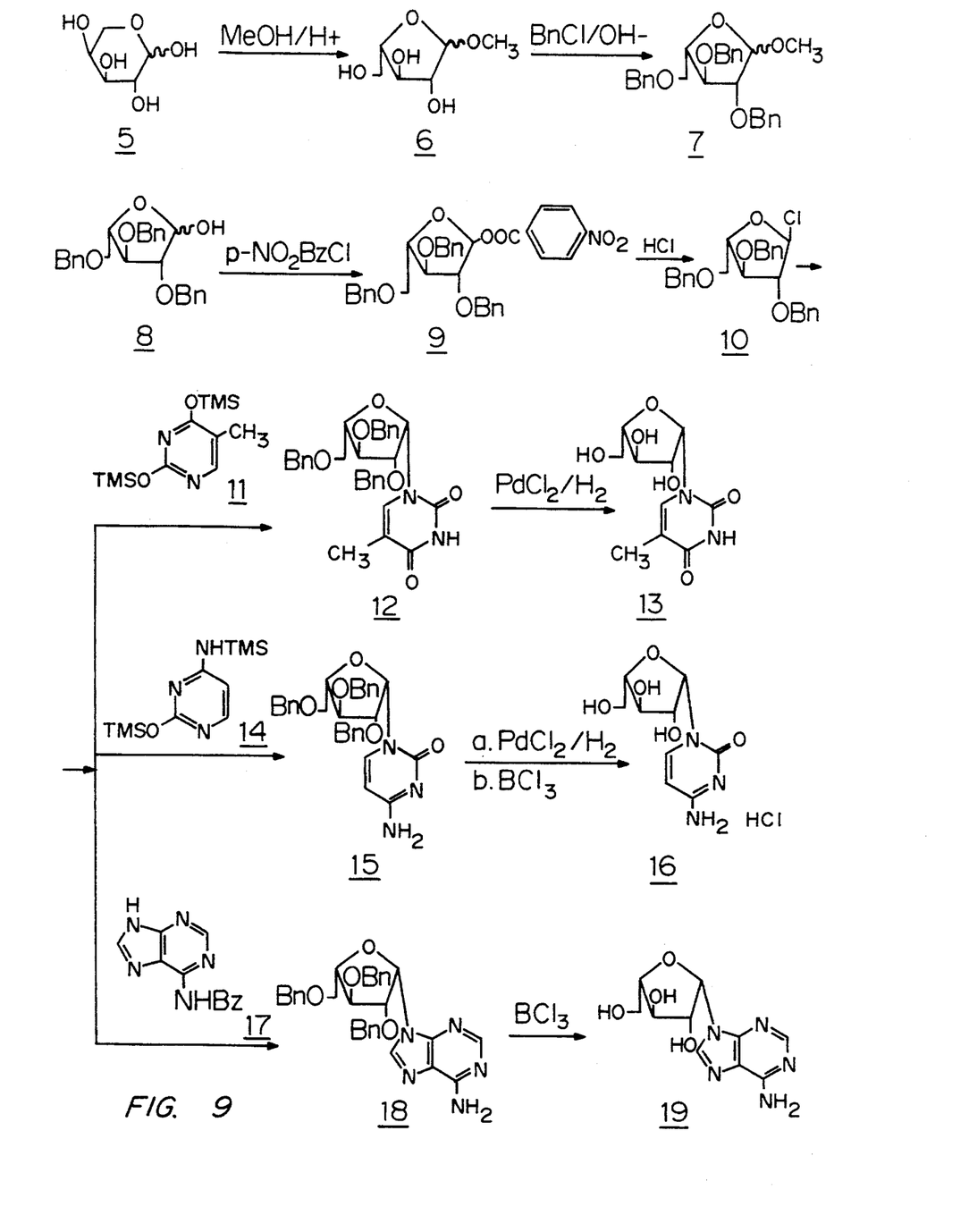
FIG. 9 is an illustration of a method for the preparation of 9-β-L-arabinofuranosyladenine.

As illustrated in FIG. 9, thirty grams (0.2 mol) of powdered L-arabinose (5) and then 0.4 ml of concentrated sulfuric acid were added to 600 ml (14.8 moles) of anhydrous methanol. The suspension was stirred, and heated under gentle reflux to give a clear solution for 2 hrs. The reaction mixture was neutralized with 1.5 g sodium hydrogen carbonate, dried ($Na_2SO_4$), and then evaporated in vacuo to give a heavy syrup 6 which was diluted with 50 ml of freshly purified tetrahydrofuran and reconcentrated (35°–40° bath) to remove residual methanol. Freshly purified tetrahydrofuran (400 ml) was added, and the mixture treated with 30 g. of Drierite, 156 g (2.78 mole) of potassium hydroxide, and 200 ml (1.74 mole) of benzyl chloride. The mixture was heated under gentle reflux overnight, cooled, filtered through a thin layer of Celite, and concentrated in vacuo, finally at high vacuo and 100° (bath). The crude, syrupy methyl 2,3,5-tri-O-benzyl-L-arabinoside (7) was dissolved in 400 ml of glacial acetic acid. The hydrolysis mixture is heated at 65°–70° for 2 hrs, concentrated in vacuo to one-third its volume, and poured into 2.5 L of a mixture of ice water. After being seeded (seeded crystals were originally obtained by chromatography being eluted with dichloromethane), the mixture was kept at 5° overnight. The aqueous layer was decant from the partially crystalline mass, and the latter was dissolved in 200 ml of dichloromethane. The solution was washed with cold, aqueous sodium hydrogen carbonate, dried ($Na_2SO_4$), filtered through a thin bed of decolorizing carbon, and concentrated in vacuo to a thin syrup which was dissolved in 200 ml of cyclohexane. After being seeded[5], the solution was kept at room temperature for 1 hr. and at 5° overnight, to give 27.7 g(33.2%) of 2,3,5-tri-O-benzyl-L-arabinose (8). m.p. 68°–73° C. $[\alpha]^{25}_D$=–1.69 [C 2.01, 9:1 (v/v p-dioxane-water)] UV(MeOH) $\lambda_{max}$ 220; 300-MHz 1HNMR(CDCl$_3$) δ3.48–3.62(m,2H,H-5), 3.94–4.18(m,3H,H-2,3,4), 5.33(d, 1H,J=4.07,H-1), 5.29(s,H-1), 7.25–7.33(m,15,H-aromat).

2,3,5-Tri-O-benzyl-1-O-(p-nitrobenzoyl)-L-arabinose (9)

Compound 8 (FIG. 9) (2 g, 4.76 mmole) was dissolved in 7.5 ml of dichloromethane, and to this solution was added a solution of 0.95 g (5.1 mmoles) of p-nitrobenzoyl chloride in a mixture of 5 ml dichloromethane and 1.5 ml of pyridine. The reaction mixture was kept at room temperature overnight, and was then washed successively with 1N hydrochloric acid (2×10 ml), aqueous sodium hydrogen carbonate (2×10 ml), and water (3×30 ml). Moisture was removed with Na$_2$SO$_4$, and the solution was concentrated in vacuo to give 2.67 g (98.4%) of a mixture of the anomers of 9. mp 68°–82° C. Further purification by silica gel column chromatography(hexanes:acetone, 8:1) raise the mp to 89°–93° C.; $[\alpha]^{24}_D$=13.04(C6.8, CH$_2$Cl$_2$) UV(MeOH) $\lambda_{max}$ 215.5 and 258.5, 250 MHz 1NMR(CDCl3): δ3.54–3.69 (m, 2H, H-5), 4.06 (m, 1H, H-4'), 4.22 (m, 1H, H-3'), 4.33 (m, 1H, H-2'), 4.38–4.78 (m, 6H, benzyl CH$_2$), 6.50 (d, 1H, J=2.35, H-1), 7.23–7.36 (m, 15H, H-aromat of benzyl group), 8.01–8.25 (m, 4H, H-acromat of nitrobenzoyl group).

10(2,3,5-Tri-O-benzyl-β-L-arabinosyl)thymine (12)

Thymine 0.444 g (3.52 mmole) and ammonium sulfate (2 mg) were suspensed in hexamethyldisilazane 10 ml, which was refluxed (140° C.) overnight under argon to give a clear solution. Excess hexamethyldisilazane was removed in vacuo with avoiding of contact of moisture to give a syrup 11.

Compound 9 (1 g, 1.76 mmole) was added to 17 ml of dichloromethane presaturated with anhydrous hydrogen chloride at 0° C. After 2 h at 0° C., the precipitated p-nitrobenzoic acid (0.25 g) was removed by filtration, and the filtrate was concentrated in vacuo to a thin syrup, then kept at high vacuo pump at room temperature for 2 to give 2,3,5-tri-O-benzyl-α-L-arabinosyl chloride (10).

The compound 10 thus prepared was dissolved in 15 ml of anhydrous dichloromethane, and the solution was added to a mixture of silylated thymine (11) and 3 g of 4 A molecular sieve. The reaction mixture was stirred at room temperature under argon for 18 h. Then the reaction mixture was diluted with 50 ml of dichloromethane, and poured into 2 ml of saturated aqueous NaHCO$_3$ under vigorous stirring. White precipitate (tin hydroxide) appeared, which was filtered out on the bed of celite. The organic layer was separated from water and washed with water (3×30 ml). The aqueous layer was extracted with dichloromethane, and the combined dichoromethane layer was dried over Na$_2$SO$_4$, and then evaporated in vacuo to give a syrup which was purified by silica gel column chromatography (chloroform:methanol, 100:1) to give 12 as a syrup 0.68 g (73%). $[\alpha]^{25}_D$=56.71 (C 0.6, CH$_2$Cl$_2$). UV(MeOH) $\lambda_{max}$ 218 and 265; 300 MHz 1HNMR(CDCl$_3$): δ1.67 (d,3H,J=1.11,CH$_3$), 3.66–3.70 (m, 2H, H-5') 4.06 (m, 1H, H-4'), 4.13 (t, 1H, J=4.7, H-3'), 4.24 (t, 1H, J=4.7, H-2'), 4.41, 4.54, 4.56 (m, 6H, benzyl CH$_2$), 6.28 (d, 1H, J=5.24, H-1'), 7.15–7.33 (m, 15H, H-aromat), 7.43 (d, 1H, J=1.31, H-6).

1-β-L-arabinofuranosylthymine (13)

Palladium chloride (680 mg, 3.835 mmole) was suspended in 100 ml of methanol, and reduced by shaking with hydrogen at room temperature. A solution of 450 mg of 12 in 25 ml of methanol was then added to the acidic suspension of palladium black. The reaction mixture was shaken with hydrogen at room temperature for 38 hrs; after the catalyst had been removed, the solution was neutralized with Dowex (HCO$_3$-) to pH 7 and concentrated in vacuo to a white solid which was recrystallized with ethanol go give 13 105 mg (47.7%). m.p. 244°–249° C. $[\alpha]^{25}_D$=–91.48 (0.25, H2O); IR(KBr): 1750, 1600 cm$^{-1}$(CO); UV(MeOH): $\lambda_{max}$ 268; 300 MHz 1HNMR(DMSO-d$_6$): δ: 1.76 (s, 3H, CH$_3$), 3.62 (t, 2H, J=4.56, H-5') 3.69 (m, 1H, H-4'), 3.90 (t, 1H, J=3.88, H-3'), 3.99 (t, 1H, J=4.10, H-2'), 5.08 (br s, 1H, C'5-OH, exchangeable), 5.42 (d, 1H, J=4.24, C'2-OH or C'3-OH, exchangeable), 5.54 (d, 1H, J=5.23, C'2-OH or C'3-OH, exchangeable), 5.97 (d, 1H, J=4.64, H-1'), 7.51 (d, 1H, J=0.97, H-6), 11.26 (s, 1H, NH, exchangeable). Anal. Calcd. for C$_{10}$H$_{14}$N$_2$O$_6$; C, 46.51; H, 5.46; N, 10.85; found: C, 46.67; H, 5.63; N, 10.56.

1-(2,3,5-Tri-O-benzyl-β-L-arabinosyl)cytosine (15)

Cytosine 0.61 g (6 mmole) and ammonium sulfate (2 mg) were suspended in hexamethyldisilazane 15 ml, which was refluxed (140° C.) under nitrogen for 2 h to give a clear solution. The silylated cytosine mixture was evaporated to dryness in vacuo with avoiding of contact with moisture to give a syrup 14.

Compound 9 (2.82 g, 5 mmole) was added to 47 ml of dry dichloromethane presaturated with anhydrous hydrogen chloride at 0° C. After 2 h at 0° C., the precipitated p-nitrobenzoic acid (0.807 g) was removed by filtration, and the filtrate was concentrated in vacuo to give syrupy 2,3,5-tri-O-benzyl-α-L-arabinosyl chloride (10).

The compound 10 thus prepared was dissolved in 28.5 ml of anhydrous dichloromethane, and the solution was added to a mixture of silylated cytosine (14) and 8.3 g of 4 A molecular sieve. The reaction mixture was stirred at room temperature under nitrogen for 5 days. Then the reaction mixture was diluted with 50 ml of dichloromethane and 20 ml of water, and poured into 2 ml of saturated aqueous NaHCO$_3$ under vigorous stirring. White precipitate (tin hydroxide) appeared, which was filtered out on the bed of celite. The organic layer was separated from water and washed with water (3×30 ml). The aqueous layer was extracted with dichloromethane, and the combined dichloromethane layer was dried over Na$_2$SO$_4$, and then evaporated in vacuo to give a syrup which was purified by silica gel column chromatography (chloroform: methanol, 96:4) to give 15 as a white solid which was recrystallized with 2-propanol to give 1.53 g (60%) m.p. 146°–148° C. $[\alpha]^{25}_D$= –105.2 (C1, CH$_2$Cl$_2$), UV(MeOH): $\lambda_{max}$ 211.5, $\lambda_{min}$ 272.5, pH1, pH7;λmax 211.5, $\lambda_{min}$ 284, pH9. 300 MHz 1HNMR(CDCl$_3$) δ: 3.65 (d, 2H, J=4.85, H-5'), 4.00 (t, 1H, J=3.72, H-3'), 4.11 (m, 1H, H-4'), 4.28 (m, 1H, H-2'), 4.38–4.55 (m, 6H, benzyl CH$_2$), 5.56 (d, 1H, J-7.5, H-5), 6.39 (d, 1H, J=4.59, H-1'), 7.12–7.31 (m, 15H, H-aromat), 7.63 (d, 1H, J=7.5, H-6).

1-β-L-Arabinofuranosylcytosine Hydrochloride Salt(16) by Catalytic Hydrogenation of 15

Palladium chloride (315 mg, 1.78 mmole) was suspended in 160 ml of methanol, and reduced by shaking with hydrogen at room temperature. To the acidic suspension of palladium black was then added a solution of 300 mg of 15 in 54 ml of methanol. The reaction mixture was shaken with hydrogen at room temperature for 3 h. After the catalyst had been removed, the solution was neutralized with Dowex (HCO$_3$-), concentrated in vacuo and then purified by preparative TLC (MeOH:CHCl$_3$, 3:5) to give a syrup which was dissolved in 3 ml of methanol, added 1% HCl solution in MeOH to pH$_1$, concentrated to dryness and triturated with 2-propanol to give 36 mg (22.1%) of 16. m.p. 190°–194° C. $[\alpha]^{25}_D$=–115.47 (C 0.07, H2O); UV(H2O) $\lambda_{max}$ 275, pH7; $\lambda_{max}$ 209.5, 273, pH11; $\lambda_{max}$ 280, pH1; 300 MHz 1HNMR(DMSO-d$_6$); δ3.61 (d, 2H, H-5'), 3.82 (m, 1H, H-4'), 3.93 (m, 1H, H-2' or H-3'), 4.04 (br s, 1H, H-2') or H-3'), 5.18 (br s, 1H, C5'—OH, exchangeable), 5.61 (br s, 1H, C2'—OH or C3'—OH, exchangeable), 5.67 (br s, 1H, C2'—OH or C3'—OH, exchangeable), 6.00 (d, 1H, J=4.02, H-1'), 6.01 (d, 1H, $J_{5,6}$=7.8, H-5) 7.92 (d, 1H, $J_{5,6}$=7.8, H-6), 8.49 (br s, 1H, NH, exchangeable), 9.38 (br s, 1H, NH, exchangeable).

1-β-L-Arabinofuranosylcytosine Hydrochloride Salt (16) by Treatment of Compound 15 with Boron Trichloride 5 ml of 1M boron trichloride in dichloromethane was cooled at =72° C. (Dry Ice-acetone). A solution of 15 (180 mg, 0.351 mmole) in 3 ml of dichloromethane was added slowly to the boron trichloride solution. After a total reaction time of 2.75 h, the cooling bath was removed and the solvent and gas were removed in vacuo. The residue was dissolved in cold dichloromethane (10 ml) and the solution was evaporated to dryness (3 times, until a white solid residue was obtained), cold saturated sodium hydrogen carbonate solution was added to adjust the pH to 6–7. The mixture was diluted with ethanol, treated to boiling, treated with charcoal, filtered, the filtrate was evaporated to dryness to a syrup which was dissolved 3 ml of methanol, added 1% HCl solution in methanol to pH1, concentrated to dryness and triturated with 2-propanol to give 16 66 mg (78.4%).

9-(2,3,5-Tri-O-benzyl-β-L-arabinosyl)adenine (18)

Thoroughly dried 9 (5 g, 8.8 mmole) was added to 82 ml of dichloromethane presaturated with anhydrous hydrogen chloride at 0°. After 2 h reaction at 0°, the precipitated p-nitrobenzoic acid (1.53 g) was removed by filtration, and the filtrate was concentrated in vacuo to a syrup which was then kept in full vacuo at room temperature for 2 hrs. The 2,3,5-tri-O-benzyl-α-L-arabinosyl chloride (10) thus prepared was dissolved in 50 ml of dichloromethane, and the solution was added to a mixture of 4.5 g (18.8 mmole) of dried N-benzoyladenine[5] (17) and 14.5 g of 4 A molecular sieve. The reaction mixture was stirred at room temperature for 1 week, filtered through a bed of celite, and concentrated in vacuo to a syrup which was chromatographed on silica gel using hexanes-acetone (3:1, Rf=0.22). The product was separated and concentrated in vacuo to a syrup which was dissolved and stirred with methanolic ammonia (20 ml) in a stainless-steel bomb, and heated overnight at 50°–55° C. The solution was then concentrated at reduced pressure to give a semisolid which was recrystallized from warm isopropyl alcohol to give 18 2.4 g (50.7%). m.p. 128°–129° C. $[\alpha]^{27}_D$=–20.04 (1.04, CH$_2$Cl$_2$); UV(CH$_2$Cl$_2$): $\lambda_{max}$ 213, 258.5; 250 MHz 1HNMR(CDCl$_3$): δ1.95 (br s, 1H, NH, exchangeable), 3.69 (d, 2H, J=4.82, H-5'), 4.18–4.30 (m, 6H, benzyl CH$_2$), 4.51–4.64 (m, 3H, H-2',3',4'), 5.73 (br s, 1H, NH, exchangeable), 6.52 (d, 1H, J-4.00, H-1'), 6.89–6.93, 7.17–7.37 (m, 15H, H-aromat of benzyl group), 8.17 (s, 1H, H-2 or H-8), 8.32 (s, 1H, H-2 or H-8).

9-β-L-Arabinofuranosyladenine (19)

5 ml of 1M boron trichloride in dichloromethane was cooled at –72° C. (Dry Ice-acetone). A solution of 18 (150 mg, 0.279 mmole) in 5 ml of dichloromethane was added slowly to the boron trichloride solution. After a total reaction time of 3.5 h, the cooling bath was removed, and the solvent and gas were removed in vacuo. The residue was dissolved in cold dichloromethane (10 ml) and the solution was evaporated to dryness (6 times, until a yellow solid residue was obtained). Cold saturated sodium hydrogen carbonate solution was added to adjust the pH 7–8. The mixture was diluted with ethanol, heated to boiling, the suspension filtered through celite, the filtrate was concentrated in vacuo to a syrup which was crystallized with water. 55 mg (74%) of 19 was obtained. m.p. 256°–258° C., UV (H$_2$O): $\lambda_{max}$ 259; 300 MHz 1HNMR(DMSO-d6): δ: 3.62–3.66 (m, 2H, H-5'), 3.77 (br s, 1H, H-4'), 4.13 (br s, 2H, H-2', 3'), 5.12 (t, 1H, J=5.4, C'5-OH, exchangeable), 5.54 (d, 1H, J=3.78, C'2-OH or C'3-OH, exchangeable), 5.63 (d, 1H, J=4.32, C'2-OH or C'3-OH, exchangeable), 6.25 (d, 1H, J=4.02, H-1'), 7.25 (br s, 2H, NH2, exchangeable), 8.13 (s, 1H—H-2 or H-8), 8.18 (s, 1H, H-2 or H-8).

II. Biological Activity

The compounds disclosed herein can be evaluated for activity against HBV and EBV as disclosed in detail below, or by other methods known to those skilled in the art.

EXAMPLE 1

Biological Activity Against HBV

Human hepatoma cells with HBV (2.2.15 cells) were used in the assay. These cells were grown to confluence in minimal essential medium with 10% fetal bovine serum. The media was changed at 3-day intervals. At confluence the treatment with the drugs was initiated and then continued for three days. Another addition of the same concentration of the drug was given at this point after removal of the media from the cultures and cultures maintained for an additional period of 3 days. The medium after the 6-day treatment was harvested and the viral particles precipitated by the polyethylene glycol method. The particles were subsequently digested and then processed for Southern analysis. The blots were hybridizied to an HBV-specific probe and vital DNA amounts assessed in comparison to DNA levels from cultures not treated with the drugs. The genomic DNA was digested with Hind III and subjected to Southern analysis. Levels of the episomal DNA were determined in relation to the integrated HBV DNA. The drug concentrations that cause 50% inhibition of the DNA (ID$_{50}$) as compared to the controls were calculated. The result is are summarized in Table I.

TABLE I

| | Inhibition of HBV by L-Nucleosides | | | | |
|---|---|---|---|---|---|
| Compound | Anti-HBV Activity ID$_{50}$ (μm) | MT2 CD$_{50}$ (μm) | CEM CD$_{50}$ | CD$_{50}$ (μm) | Therapeutic Index (DC$_{50}$/ID$_{50}$) |
| L-FMAU | 0.1 | 100 | >100 | 913 ± 70 | 9130 |
| D-FMAU | 2.0 | 8–9 | 10 | <10 | <5 |
| D-FEAU | 5.0 | 100 | 90 | >400 | >80 |
| L-FEAU | >5.0 | 100 | >100 | >400 | >80 |

EXAMPLE 2

Biological Activity Against EBV

H1 cells were maintained in long phase growth for two days prior to the initiation of treatment. The cells were centrifuged at 600 g for 10 min. at room temperature to separate them from the medium containing pre-existing virus particles. The H1 cells were seeded in 24 well plates at a density of 1×10$^5$ cells per well in 2 ml of fresh medium with or without drug and incubated at 37° C. for 5 days. The medium containing virion was saved and used for evaluating the inhibitory effect of drugs on virus production and infectivity by use of a bioassay. The virion were pelleted from the cell free medium by centrifugation at 45,000 rpm for 90 min. in a SW-50 Ti rotor (Beckman). The virion were resuspended in 1 ml growth medium and then used to infect $1\times10^6$ Raji cells for 48 hours. Since the level of EBV DP activity in Raji cells post superinfection is proportional to the number of virions added (unpublished result), the EBV specific DP activity induced was able to be measured. The inhibitory drug effect Was calculated by comparing the EBV DP activity to multiple dilution controls. No inhibition of mitochondrial DNA content in H1 cells was observed when the cells were treated by 1 mM L-MAU for 6 days.

Slot Blot Assay—The amount of mitochondrial DNA was measured by the slot blot method (2). $2\times10^5$ of the treated and non-treated $H_1$ cells were lysed in 200 μl of 10 mM of Tris.HCl (pH 7.5) solution by the freeze/thaw method. The cell lysate was treated with 10 μg/ml of RNase A at 37° C. for 30 min, and then proteinase K (100 μg/ml) at 55° C. for 2 hours. Equal amounts of 20×SSC buffer was added to each cell lysate. After boiling for 10 min, the samples were spotted onto nylon membranes (Hybond-N, Amersham Corp.). A radiolabelled human mitochondrial DNA fragment was used as a probe for DNA hybridization. The same membranes were reprobed with human Alu DNA after removing the mitochondrial DNA probe. The amount of mitochondrial DNA in the treated and non-treated H1 cells was quantified by densitometer (LKB Ultroscan XL).

The results are provided in Table 2.

TABLE 2

| Drugs | $CD_{50}$ (μM) | $ID_{90}$ (μM) | Therapeutic Index ($CD_{50}/ID_{90}$) |
|---|---|---|---|
| PFA | 1200 ± 100 | 75 ± 5 | 16 |
| DHPG | 75 ± 6 | 5 ± 1 | 15 |
| ACV | 1000 ± 75 | 50 ± 8 | 20 |
| PCV | 500 ± 55 | 20 ± 2 | 25 |
| Sdc28 | >50 | 0.5 ± 0.05 | >100 |
| L-FMAU | 913 ± 70 | 5 ± 0.8 | 182 |
| D-FMAU | <10 | 0.1 | <100 |
| L-FEAU | >400 | 20 | 20 |
| D-FEAU | >400 | 1 | >400 |
| L-FIAC | inactivity up to 100 μM | | |

Inhibitory effect of compounds on EBV: The $CD_{50}$ was performed by exposing H1 cells to different concentrations of the compounds in normal growth medium at 37° C. for 72 hours; the cells were then counted and compared with controls. H1 cells were treated for 5 days and the $ID_{90}$ was determined by bioassay.

IV. Preparation of Pharmaceutical Compositions

The compounds disclosed herein and their pharmaceutically acceptable salts, prodrugs, and derivatives, are useful in the prevention and treatment of HBV and EBV infections and other related conditions such as anti-HBV or anti-EBV antibody positive and HBV- or EBV-positive conditions, chronic liver inflammation caused by HBV, cirrhosis, acute hepatitis, fulminant hepatitis, chronic persistent hepatitis, and fatigue. These compounds or formulations can also be used prophylactically to prevent or retard the progression of clinical illness in individuals who are anti-HBV anti-EBV antibody or HBV- or EBV-antigen positive or who have been exposed to HBV or EBV.

Humans suffering from any of these conditions can be treated by administering to the patient an effective HBV- or EBV-treatment amount of one or a mixture of the active compounds described herein or a pharmaceutically acceptable derivative or salt thereof, optionally in a pharmaceutically acceptable carrier or diluent. The active materials can be administered by any appropriate route, for example, orally, parenterally, intravenously, intradermally, subcutaneously, or topically, in liquid or solid form.

The active compound is included in the pharmaceutically acceptable carrier or diluent in an amount sufficient to deliver to a patient a therapeutically effective amount without causing serious toxic effects in the patient treated.

A preferred dose of the active compound for all of the above-mentioned conditions will be in the range from about 1 to 60 mg/kg, preferably 1 to 20 mg/kg, of body weight per day, more generally 0.1 to about 100 mg per kilogram body weight of the recipient per day. The effective dosage range of the pharmaceutically acceptable derivatives can be calculated based on the weight of the parent nucleoside to be delivered. If the derivative exhibits activity in itself, the effective dosage can be estimated as above using the weight of the derivative, or by other means known to those skilled in the art. In one embodiment, the active compound is administered as described in the product insert or Physician's Desk Reference for 3'-azido-3'-deoxythymidine (AZT), 2',3'-dideoxyinosine (DDI), 2',3'-dideoxycytidine (DDC), or 2',3'-dideoxy-2',3 '-didehydrothymidine (D4T) for HIV indication.

The compound is conveniently administered in unit any suitable dosage form, including but not limited to one containing 7 to 3000 mg, preferably 70 to 1400 mg of active ingredient per unit dosage form. A oral dosage of 50–1000 mg is usually convenient.

Ideally the active ingredient should be administered to achieve peak plasma concentrations of the active compound of from about 0.2 to 70 μM, preferably about 1.0 to 10 μM. This may be achieved, for example, by the intravenous injection of a 0.1 to 5% solution of the actiive ingredient, optionally in saline, or administered as a bolus of the active ingredient.

The active compound can be provided in the form of pharmaceutically acceptable salts. As used herein, the term pharmaceutically acceptable salts or complexes refers to salts or complexes of the nucleosides that retain the desired biological activity of the parent compound and exhibit minimal, if any, undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid; (b) base addition salts formed with cations such as sodium, potassium, zinc, calcium, bismuth, barium, magnesium, aluminum, copper, cobalt, nickel, cadmium, sodium, potassium, and the like, or with an organic cation formed from N,N-dibenzylethylene-diamine, ammonium, or ethylenediamine; or (c) combinations of(a) and (b); e.g., a zinc tannate salt or the like.

Modifications of the active compound, specifically at the $N^6$ or $N^4$ and 5'—positions, can affect the bioavailability and rate of metabolism of the active species, thus providing control over the delivery of the active species.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to,the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound, or pharmaceutically acceptable derivative or salt thereof can also be mixed with other active materials that do not impair the desired action, or with materials that supplement the desired action, such as antibiotics, antifungals, antiinflammatories, or other antivirals, including anti-HBV, anti-EBV, anti-cytomegalovirus, or anti-HIV or anti-EBV agents.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS). In a preferred embodiment, he active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

This invention has been described with reference to its preferred embodiments. Variations and modifications of the invention, will be obvious to those skilled in the art from the foregoing detailed description of the invention. It is intended that all of these variations and modifications be included within the scope of the appended claims.

We claim:

1. A method for the treatment of a human infected with HBV comprising administering to said human an HBV treatment amount of an L-nucleoside of the formula:

wherein R is selected from the group consisting of 5-methyluracil, adenine and cytosine, and R' is hydrogen, acyl, alkyl or a monophosphate, diphosphate or triphoshate ester.

2. The method of claim 1, wherein the L-nucleoside is 2'-fluoro-5-methyl-β-L-arabinofuranosyluridine.

3. The method of claim 1, wherein the L-nucleoside is at least 95% free of the corresponding D-nucleoside.

4. The method of claim 1, wherein R' is hydrogen.

5. The method of claim 3, wherein R' is hydrogen.

6. The method of claim 1, wherein R' is selected from the group consisting of monophosphate, diphosphate and triphosphate.

7. The method of claim 3, wherein R' is selected from the group consisting of monophosphate, diphosphate and triphosphate.

8. The method of claim 1, wherein R is 5-methyluracil.

9. The method of claim 8, wherein R' is hydrogen.

10. The method of claim 3, wherein R is 5-methyluracil.

11. The method of claim 10, wherein R' is hydrogen.

12. The method of claim 2, wherein the L-nucleoside is at least 95% free of the corresponding D-nucleoside.

13. The method of claim 1 or 3, wherein R is adenine.

14. The method of claim 1 or 3, wherein R is cytosine.

15. The method of claim 12, wherein R' is hydrogen.

16. The method of claim 13, wherein R' is hydrogen.

17. The method of claim 1 or 3, wherein R is 5-methyluracil and R' is a phosphate esterr.

18. The method of claim 13, wherein R' is a phosphate ester.

19. The method of claim 1 wherein the nucleoside is administered orally.

20. The method of claim 2, wherein the nucloeside is administered orally.

21. The method of claim 3, wherein the nucleoside is administered orally.

22. The method of claim 12, wherein the nucleoside is administered orally.

23. The method of claim 1, wherein the nucleoside is administered in a liposomal suspension.

24. The method of claim 2, wherein the nucleoside is administered in a liposomal suspension.

25. The method of claim 3, wherein the nucleoside is administered in a liposomal suspension.

26. The method of claim 12, wherein the nucleoside is administered in a liposomal suspension.

27. The method of claim 12 or 13, wherein the nucleoside is administered in a liposomal suspension.

28. A method for the treatment of a human infected with HBV comprising administering to said human an HBV treatment amount of pharmaceutically acceptable salt of an L-nucleoside of the formula:

wherein R is selected from the group consisting of 5-methyluracil, adenine and cytosine, and R' is hydrogen, acyl, or alkyl or a monophosphate, diphosphate or triphosphate ester.

29. The method of claim 1, wherein the nucleoside is administered in a controlled release formulation.

30. The method of claim 2, wherein the nucleoside is administered in a controlled release formulation.

31. The method of claim 3, wherein the nucleoside is administered in a controlled release formulation.

32. The method of claim 12, wherein the nucleoside is administered in a controlled release formulation.

* * * * *